(12) United States Patent
Sato

(10) Patent No.: US 10,143,470 B2
(45) Date of Patent: Dec. 4, 2018

(54) TISSUE-FASTENING TOOL INDWELLING DEVICE

(71) Applicant: OLYMPUS CORPORATION, Tokyo (JP)

(72) Inventor: Masatoshi Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/822,916

(22) Filed: Nov. 27, 2017

(65) Prior Publication Data

US 2018/0078252 A1 Mar. 22, 2018

Related U.S. Application Data

(63) Continuation of application No. PCT/JP2016/050241, filed on Jan. 6, 2016.

(51) Int. Cl.
*A61B 17/10* (2006.01)
*A61B 17/064* (2006.01)
(Continued)

(52) U.S. Cl.
CPC ............ *A61B 17/064* (2013.01); *A61B 17/10* (2013.01); *A61B 17/11* (2013.01);
(Continued)

(58) Field of Classification Search
CPC .................. A61B 17/1114; A61B 17/11; A61B 17/00234; A61B 17/0644; A61B 17/3468;
(Continued)

(56) References Cited

U.S. PATENT DOCUMENTS

2010/0010508 A1 1/2010 Takahashi et al.
2010/0010514 A1* 1/2010 Ishioka .............. A61B 17/0644
606/151
(Continued)

FOREIGN PATENT DOCUMENTS

EP 2499975 A1 9/2012
JP 2010-017541 A 1/2010
(Continued)

OTHER PUBLICATIONS

International Search Report dated Mar. 22, 2016 issued in PCT/JP2016/050241.

*Primary Examiner* — Elizabeth Houston
*Assistant Examiner* — Mohamed Gabr
(74) *Attorney, Agent, or Firm* — Scully, Scott, Murphy & Presser, P.C.

(57) ABSTRACT

A tissue-fastening tool indwelling device includes: a sheath; a needle tube having a needle tip and disposed to be retractable from a distal end of a lumen of the sheath; a tissue-fastening tool having a restoring force to a curved shape with distal and proximal end side regions and disposed inside the needle tube in a stretched state; and a stylet coupled to a proximal end portion of the tissue-fastening tool in the needle tube. The stylet has a first state in which the stylet is advanced straight with respect to the needle tube and the sheath until the entire distal end side region of the tissue-fastening tool protrudes from the needle tube, and a second state in which the stylet is advanced while being rotated until a proximal end of the proximal end side region of the tissue-fastening tool protrudes from the needle tube.

14 Claims, 28 Drawing Sheets

(51) Int. Cl.
*A61B 17/11* (2006.01)
*A61B 17/34* (2006.01)
*A61B 17/00* (2006.01)

(52) U.S. Cl.
CPC ...... *A61B 17/1114* (2013.01); *A61B 17/3468* (2013.01); *A61B 2017/00867* (2013.01); *A61B 2017/0649* (2013.01)

(58) Field of Classification Search
CPC .. A61B 2017/0649; A61B 2017/00867; A61B 2017/00862; A61B 2017/0645; A61B 2017/1139; A61B 2017/00477; A61B 1/018; A61F 2002/041; A61F 2002/044; A61F 2/88
See application file for complete search history.

(56) References Cited

U.S. PATENT DOCUMENTS

2012/0029278 A1* 2/2012 Sato ................ A61B 17/00234
600/104
2013/0144164 A1 6/2013 Sato

FOREIGN PATENT DOCUMENTS

| WO | WO 02/19923 A1 | 3/2002 |
| WO | WO 2011/055700 A1 | 5/2011 |
| WO | WO 2015/191465 A1 | 12/2015 |

\* cited by examiner

TISSUE-FASTENING TOOL INDWELLING DEVICE

FIELD OF THE INVENTION

The present invention relates to a tissue-fastening tool indwelling device. This application is a continuation application based on PCT Patent Application No. PCT/JP2016/050241, filed Jan. 6, 2016, the content of which is incorporated herein by reference.

DESCRIPTION OF RELATED ART

In the past, instruments and methods for fastening of tissue in the body have been known. For example, an instrument for pushing a fastener out of a needle and fastening the fastener to tissue is disclosed in PCT International Publication No. WO2002/019923 Specification. In the tissue fastening instrument, a stopper for controlling a depth when the needle punctures the tissue and an amount by which the fastener is supplied to the tissue is provided. When a procedure is performed using the tissue fastening instrument, the instrument in which the fastener and the needle are stored pushes onto the tissue. When the needle is advanced and punctures the tissue, a position of the fastener is fixed by the stopper. Afterwards, the needle is pulled out of the tissue. Since the fastener does not move due to the presence of the stopper, a distal end portion thereof is left behind inside the tissue. When the tissue fastening instrument is removed from the tissue, the rest (the proximal end portion) of the fastener remains outside the tissue. When the fastener is restored to a coil shape, the tissue is fixed.

SUMMARY OF THE INVENTION

According to a first aspect of the present invention, a tissue-fastening tool indwelling device includes: a sheath in which a lumen is formed; a needle tube having a needle tip, formed in a tubular shape, and disposed to be projectable and retractable from a distal end of the lumen; a tissue-fastening tool having a restoring force for restoration to a curved shape with distal and proximal end side regions and disposed inside the needle tube in a stretched state; and a stylet coupled to a proximal end portion of the tissue-fastening tool in the needle tube. The stylet has: a first state in which the stylet is advanced straight with respect to the needle tube and the sheath until the entire distal end side region of the tissue-fastening tool protrudes from the needle tube; and a second state in which the stylet is advanced while being rotated until a proximal end of the proximal end side region of the tissue-fastening tool protrudes from the needle tube after the stylet advanced with respect to the needle tube and the sheath.

According to a second aspect of the present invention, the tissue-fastening tool indwelling device according to the first aspect may include: a needle slider configured to advance and retract the needle tube; a first manipulation input part fixed to the needle slider in an advancing-retracting direction and configured to be rotatable with respect to the needle slider; an intermediate member configured to advance with respect to the needle slider and configured to make the stylet to advance straight, in accordance with rotation of the first manipulation input part with respect to the needle slider; and a restriction portion formed at the intermediate member and configured to restrict the rotation of the first manipulation input part. In a restricted state in which the rotation of the first manipulation input part is restricted by the restriction portion, a distal end of the tissue-fastening tool may protrude from the needle tip, and a proximal end of the tissue-fastening tool may be located in the needle tube.

According to a third aspect of the present invention, in the tissue-fastening tool indwelling device according to the second aspect, an outer circumference of the intermediate member may have a step that helically extends between a proximal end and distal end of the intermediate member; the first manipulation input part may have a sliding portion that is slidable while being engaged with the step; a proximal end face maybe formed at a terminal side of the step in a proximal end side of the intermediate member; and the restricted state may be a state in which the sliding portion of the first manipulation input part abuts against the proximal end face and thereby the stylet may be restricted not to be advanced.

According to a fourth aspect of the present invention, in the tissue-fastening tool indwelling device according to the second aspect, an outer circumference of the intermediate member may have a helical step that extends between a proximal end and distal end of the intermediate member; the first manipulation input part may have a sliding portion that is slidable while being engaged with the step; a proximal end face may be formed at a terminal side of the step in a proximal end side of the intermediate member; a locking surface may be formed at closer to a distal end side of the intermediate member than the proximal end face; and the restricted state may be a state in which, the sliding portion of the first manipulation input part enters between the locking surface and the proximal end face, and thereby the stylet may be restricted not to be advanced and retracted.

According to a fifth aspect of the present invention, the tissue-fastening tool indwelling device according to the first aspect may include: a first manipulation input part that straightly advances the stylet with respect to the needle tube and the sheath; and a second manipulation input part that advances the stylet while rotating the stylet with respect to the needle tube.

According to a sixth aspect of the present invention, the tissue-fastening tool indwelling device according to the fifth aspect may include: a cam tube that has a first helical groove which is formed helically on a wall surface of a cylinder and into which a proximal end region of the stylet is inserted; the intermediate member having a distal end face fixed to a proximal end portion of the cam tube; a guided part that is located at closer to a distal side than the distal end face of the intermediate member, and protrudes outward from an outer circumferential surface of the proximal end region of the stylet in a radial direction, the guided part being slidably engaged with the first helical groove; and a guide member that has a slit surface forming a slit extending along a longitudinal axis of the stylet in a linear shape to be engaged with the guided part, that is relatively rotatable around a central axis of the needle tube with respect to the needle tube, and that is fixed to a proximal end portion of the needle tube in a direction of the central axis of the needle tube. In the first state, the stylet may straightly advance the tissue-fastening tool into the needle tube depending on input to the first manipulation input part, and in the second state, the stylet may cause the guided part to slide along the first helical groove depending on input to the second manipulation input part and may advance the tissue-fastening tool while rotating the tissue-fastening tool in the needle tube.

According to a seventh aspect of the present invention, the tissue-fastening tool indwelling device according to the first aspect may include: a cam tube that has a first helical groove which is formed helically on a wall surface of a cylinder and into which a proximal end region of the stylet is inserted; an intermediate member having a distal end face fixed to a proximal end portion of the cam tube; a guided part that is located at closer to a distal side than the distal end face of the intermediate member, protrudes outward from an outer circumferential surface of the proximal end region of the stylet in a radial direction, and is slidably engaged with the first helical groove; and a guide member that has a slit surface forming a slit extending along a longitudinal axis of the stylet in a linear shape to be engaged with the guided part, that is relatively rotatable around a central axis of the needle tube with respect to the needle tube, and that is fixed to a proximal end portion of the needle tube in a direction of the central axis of the needle tube. In the first state, the guided part may come into contact with the distal end face of the intermediate member, and as the guided part is pushed out by the distal end face of the intermediate member, the stylet may be straightly advanced with respect to the needle tube and the sheath while causing the guided part to slide along the slit surface. In the second state, the guided part may be separated from the distal end face of the intermediate member, and as the stylet is rotated while being advanced with respect to the intermediate member, the guided part may rotate while engaged with the slit surface in a rotational direction of the stylet and while causing the guided part to slide along the first helical groove of the cam tube, and the guided part may advance the stylet while rotating the stylet with respect to the needle tube.

According to an eighth aspect of the present invention, the tissue-fastening tool indwelling device according to the seventh aspect may include: a needle slider fixed to the guide member with respect to a direction of a longitudinal axis of the guide member so as to be rotatable with respect to the guide member; a main manipulation part main body provided between the guide member and the needle slider in a radial direction of the needle slider and having an outer circumferential surface in which a second helical groove formed in a helical shape is formed; and a slide button unit having a base body and a locking part that protrudes inward in a radial direction of the base body to be engaged with the second helical groove. A dent portion may be formed at a proximal end of the second helical groove, and the locking part may be fitted into the dent portion and be locked in a helical direction of the second helical groove.

According to a ninth aspect of the present invention, the tissue-fastening tool indwelling device according to the seventh aspect may include: a needle slider fixed to the guide member with respect to a direction of a longitudinal axis of the guide member so as to be rotatable with respect to the guide member; and a first manipulation input part that straightly advances the stylet with respect to the needle tube and the sheath. The first manipulation input part may be a rotation knob that is rotatable with respect to the needle slider; the rotation knob may have a projection protruding inward in a radial direction from an inner circumference thereof; a third helical groove and a first locking surface that formed at a proximal end portion of the third helical groove may be provided with an outer circumference of the intermediate member, the third helical groove into which the projection slides while being engaged with the third helical groove; and if an external force toward the proximal end side is applied to the intermediate member when the projection is located at closer to a proximal side of the third helical groove than the first locking surface, the first locking surface locks the projection.

According to a tenth aspect of the present invention, the tissue-fastening tool indwelling device according to the seventh aspect may include: a needle slider fixed to the guide member with respect to a direction of a longitudinal axis of the guide member so as to be rotatable with respect to the guide member; and a first manipulation input part that straightly advances the stylet with respect to the needle tube and the sheath. The first manipulation input part may be a rotation knob that is rotatable with respect to the needle slider; the rotation knob may have a projection protruding inward in a radial direction from an inner circumference thereof; a third helical groove and a second locking surface formed at a distal end portion of the third helical groove may be provided with an outer circumference of the intermediate member, the third helical groove into which the projection slides while being engaged with the third helical groove; and if an external force toward the distal end side is applied to the intermediate member when the projection is located at closer to a distal end side of the third helical groove than the second locking surface, the second locking surface locks the projection.

According to an eleventh aspect of the present invention, the tissue-fastening tool indwelling device according to the fifth aspect may include: a second cam tube that has an outer circumferential surface in which a fourth helical groove helically formed in a wall surface of a cylinder is formed, and has an end portion of the fourth helical groove on the outer circumferential surface; and a fitting hole which is formed in a region between grooves for the fourth helical groove on the outer circumferential surface of the second cam tube, the fitting hole into which a rod-like member is fittable. The second manipulation input part may be a rotation handle having a second engaging part that protrudes inward from an inner circumferential surface thereof in a radial direction and that is slidably fitted into the fourth helical groove. When the second engaging part is locked on an end portion of the fourth helical groove of the second cam tube, the fitting hole is exposed at a position closer to a distal side of the second cam tube than a distal end of the rotation handle.

According to a twelfth aspect of the present invention, in the tissue-fastening tool indwelling device according to the fifth aspect, a maximum movable amount of the stylet in a direction along a longitudinal axis of the sheath due to manipulation of the first manipulation input part may be set to be smaller than the maximum movable amount of the stylet in the direction along the longitudinal axis of the sheath due to manipulation of the second manipulation input part.

DETAILED DESCRIPTION OF THE PREFERRED EMBODIMENTS

A tissue-fastening tool indwelling device (hereinafter referred to simply as an "indwelling device") according to an embodiment of the present invention will be described.

Figure 1:
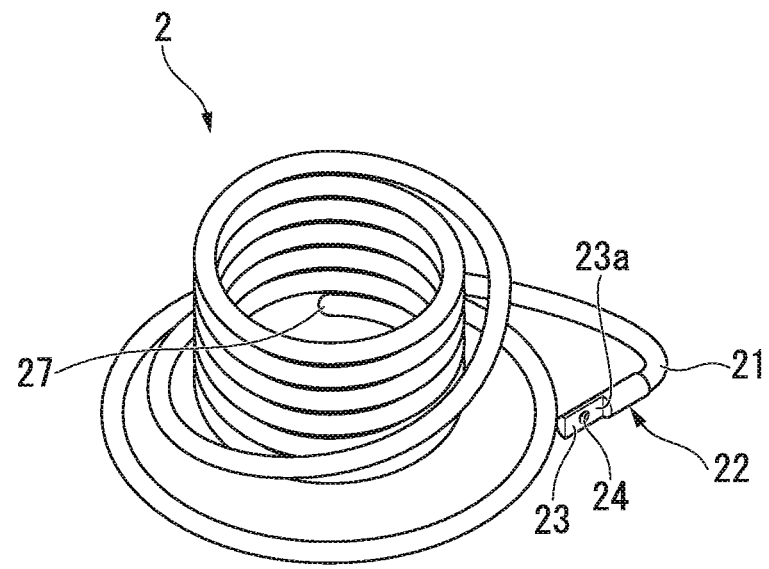
FIG. 1 is a perspective view representing an example of an implant according to an embodiment of the present invention.
Figure 2:
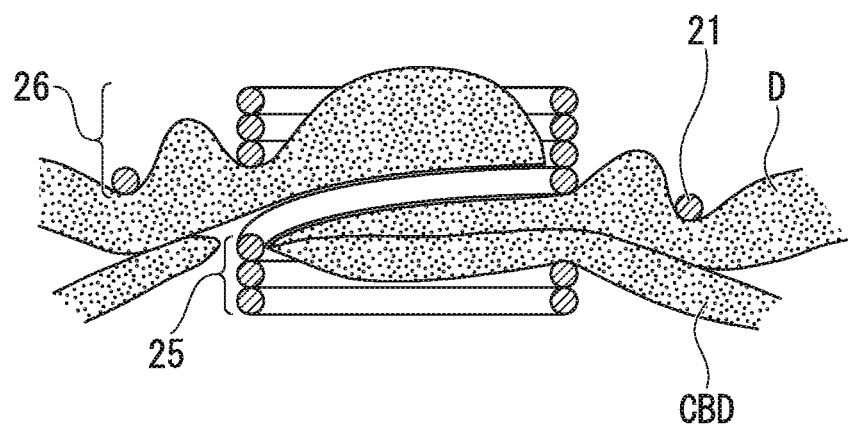
FIG. 2 is a diagram representing an example of a usage mode of the implant of the embodiment of the present invention.

First, an implant which is loaded in an implant-indwelling device 1 and indwelled in the body will be described. As the implant, it is possible to use a known implant which is made of a highly elastic metal wire material having a distal end side region and a proximal end side region, has a curved shape in advance, is elastically deformable, and has a restoring force restoring the implant to the curved shape. In the present embodiment, as represented in FIG. 1, an example (see FIGS. 20 to 26) is represented in which a tissue-fastening tool 2 that is formed by winding one shape memory wire in a coil shape and that sandwiches and anastomoses two luminal tissues of a tissue D of a duodenum and a tissue CBD of a common bile duct in a close-contact state as represented in FIG. 2 is indwelled as an implant.

The tissue-fastening tool (a treatment part) 2 includes an implant-coupling part (a coupling part) 22 at a proximal end 21 thereof. As represented in FIG. 1, the implant-coupling part 22 has a first engagement part main body 23 and a recessed part 24. The first engagement part main body 23 has a semicircular pillar-shaped part obtained by cutting a cylinder in half along a central axis thereof. The recessed part 24 is a hole formed to extend in a perpendicular direction from a planar part 23a parallel to a longitudinal axis of the first engagement part main body 23. The implant-coupling part 22 is configured to be engageable with a stylet to be described later.

Figure 3:
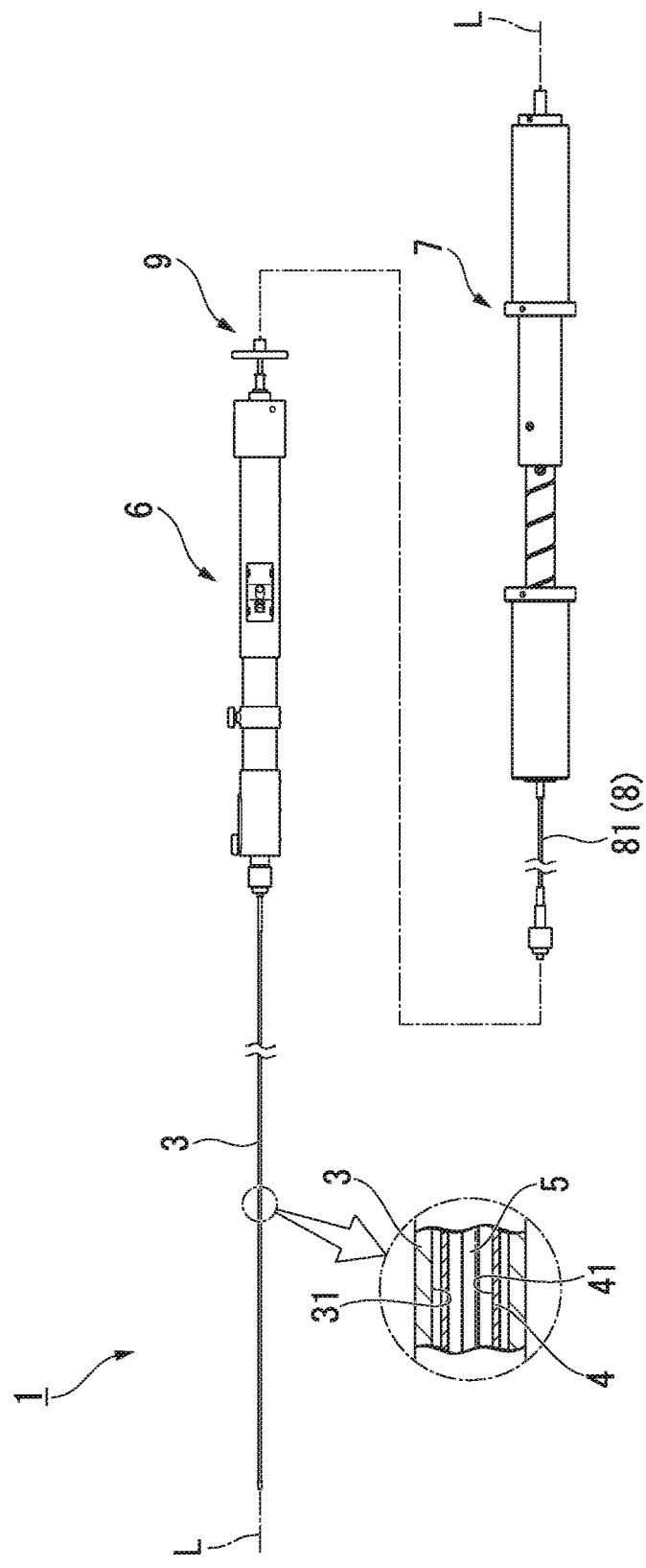
FIG. 3 is an overall diagram representing an endoscopic treatment tool according to the embodiment of the present invention.

FIG. 3 is an overall diagram representing the indwelling device 1 according to this embodiment. The indwelling device 1 is a device for indwelling the tissue-fastening tool 2 in a body using an endoscope. The indwelling device 1 has a sheath 3, a needle tube (an elongated shaft and a treatment part) 4, a stylet (a treatment part) 5, a main manipulation part (a first manipulation part) 6, an auxiliary manipulation part (a second manipulation part) 7, and a manipulation transmission member (hereafter, referred to as a "transmission member" in some cases) 8. The sheath 3, the needle tube 4, the stylet 5, and the main manipulation part 6 are disposed on a central axis L of the sheath 3. The auxiliary manipulation part 7 is coupled to the main manipulation part 6 on the central axis L of the sheath 3. In the following description of the main manipulation part 6 and the auxiliary manipulation part 7, the term "central axis" is used with a meaning including an extension line of the central axis L of the sheath 3 when the main manipulation part 6 and the auxiliary manipulation part 7 are disposed on the central axis L of the sheath 3.

Figure 4:
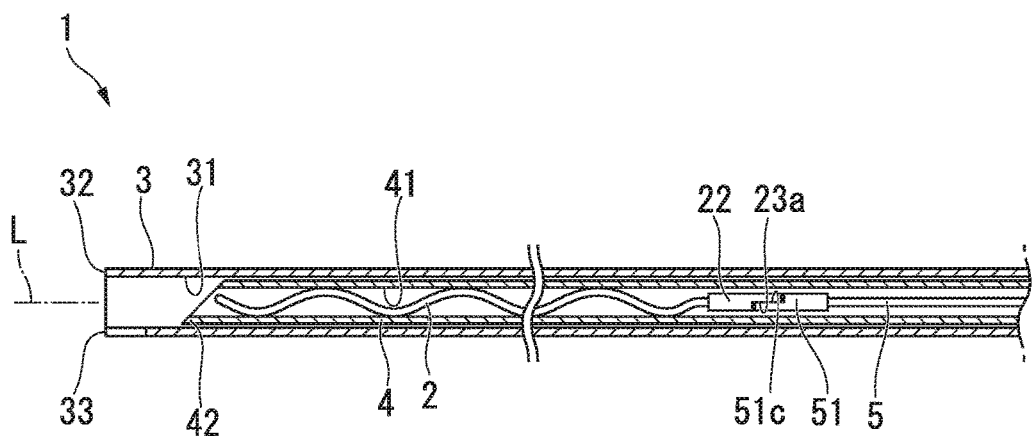
FIG. 4 is a cross-sectional view of a distal end portion of the endoscopic treatment tool according to the embodiment of the present invention.

FIG. 4 is a cross-sectional view of a distal end portion of the indwelling device 1. The sheath 3 is a part which is inserted into a body. As represented in FIGS. 3 and 4, a lumen 31 is formed inside the sheath 3 and extends from a distal end thereof to a proximal end thereof. As represented in FIG. 4, a notched part 33 extending in a direction of the central axis L is formed in a distal end opening portion 32 of the sheath 3. The needle tube 4 to be described later is inserted into the sheath 3 so as to freely advance and retract. A proximal end side of the sheath 3 is connected to the main manipulation part (the manipulation part) 6. The sheath 3 is inserted into a treatment tool channel 102 of an endoscope insertion part 101 (see FIG. 20).

As represented in FIG. 4, the needle tube 4 is a long member having a hollow needle tube insertion passage (an insertion passage) 41. The needle tube 4 is inserted into the lumen 31 to be projectable and retractable from a distal end of the sheath 3. A distal end (a puncturing part, a needle tip) 42 of the needle tube 4 is formed to be sharp and functions as a puncture needle. A proximal end of the needle tube 4 is attached to a distal end of a needle guide 67 (see FIG. 6A), which will be described later, to be relatively rotatable and immovable forward and backward. That is, the needle guide 67 is freely rotate around the central axis L with respect to the needle tube 4 and fixed to the direction of the central axis with respect to the needle tube. In other words, the needle guide 67 is fixed to the needle tube 4 in the central axis L and the needle guide 67 is configured to be rotatable with respect to the needle tube 4. A superelastic alloy represented by a nickel titanium alloy or stainless steel can be adopted, for example, as a material of the needle tube 4.

The stylet 5 is a long core material, a distal end portion thereof is located inside the needle tube insertion passage 41 (see FIG. 3), and a proximal end portion thereof extends to the main manipulation part 6 provided on the proximal end side of the sheath 3. The stylet 5 is a member which advances and retracts the tissue-fastening tool 2 with respect to the needle tube insertion passage 41. The stylet 5 is configured to be projectable and retractable from the distal end of the sheath 3.

Figure 7:
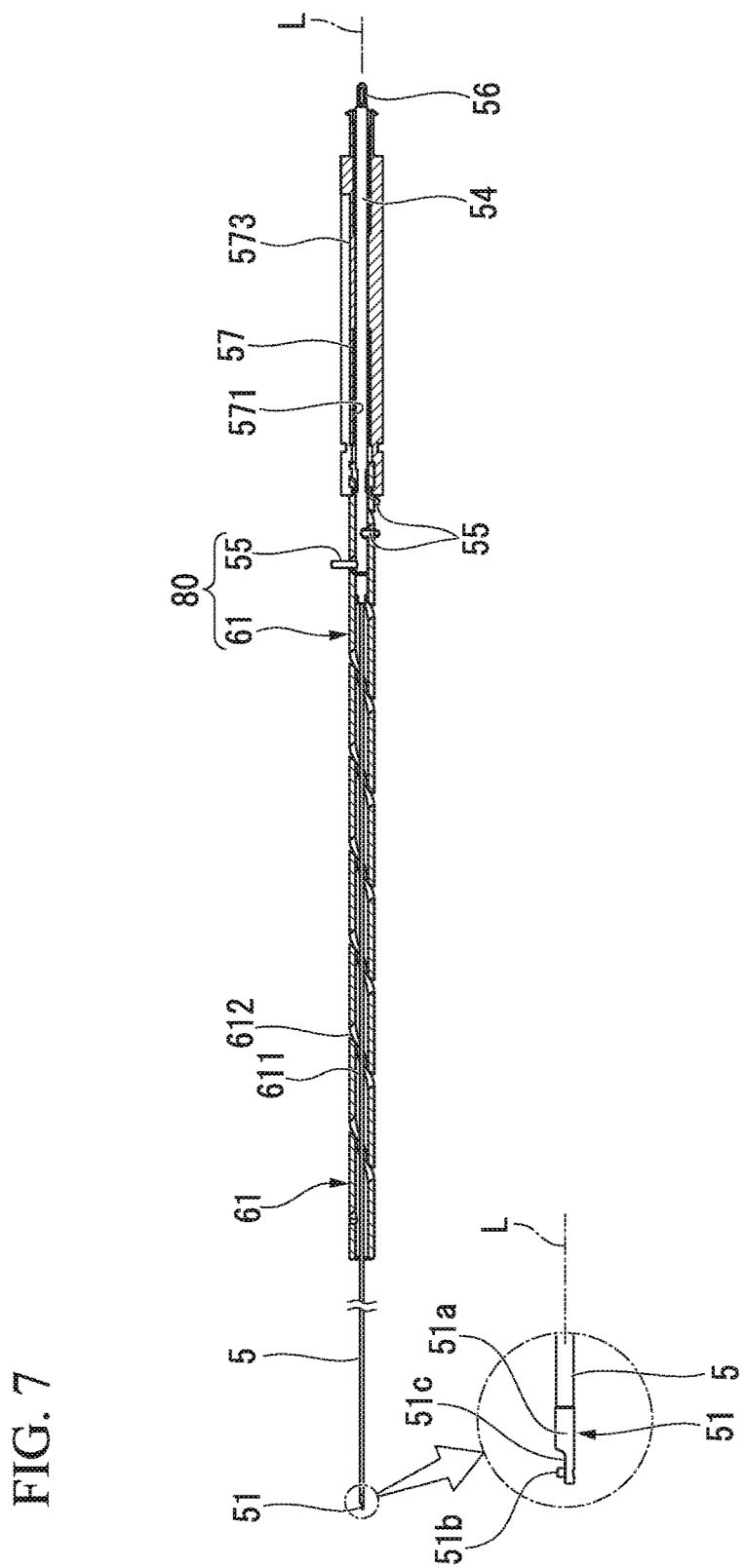
FIG. 7 is a cross-sectional view of a stylet and a first cam tube according to the embodiment of the present invention.

FIG. 7 is a cross-sectional view of the stylet 5 and a first cam tube (a cam tube) 61. As represented in FIG. 7, a distal end engagement part 51 is provided at a distal end portion of the stylet 5. The distal end engagement part 51 has a second engagement part main body 51a and a protruding part 51b. A proximal end portion of the second engagement part main body 51a has a cylindrical shape, and a distal end portion thereof has a semi-cylindrical shape in which a cylinder is cut in half on the central axis L. The protruding part 51b is formed to protrude in a perpendicular direction from a planar part 51c of the second engagement part main body 51a parallel to the central axis L. As represented in FIG. 4, when the planar parts 23a and 51c come into contact with each other inside the needle tube 4 and the protruding part 51b is inserted into the recessed part 24, the distal end engagement part 51 and the implant-coupling part 22 (a proximal end part of the tissue tissue-fastening tool 2) engage with each other and the tissue-fastening tool 2 is coupled to the stylet 5.

As represented in FIG. 7, a stylet proximal end member 54 is fixed to a proximal end portion of the stylet 5. Three first engaging pins (cam followers, first projections, and guided part) 55 are provided at a distal end portion of the stylet proximal end member 54 to protrude in an orthogonal direction (outwardly in a radial direction) to the central axis L from an outer circumference thereof. The three first engaging pins 55 are provided to be spaced part at an equal angle in a circumferential direction and spaced apart at an equal interval in the direction of the central axis L.

Figure 6A:
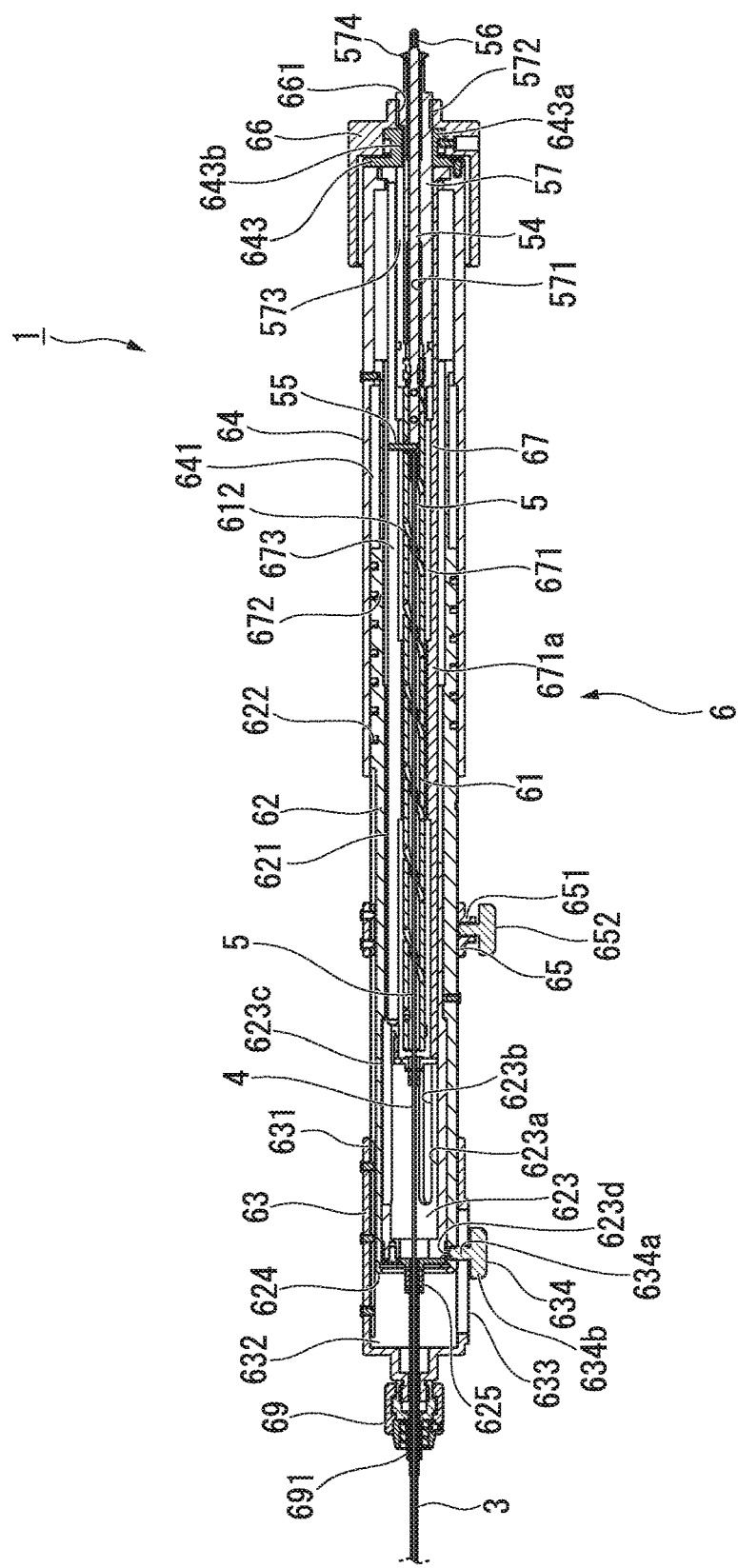
FIG. 6A is a cross-sectional view of the main manipulation part according to the embodiment of the present invention.
Figure 6B:
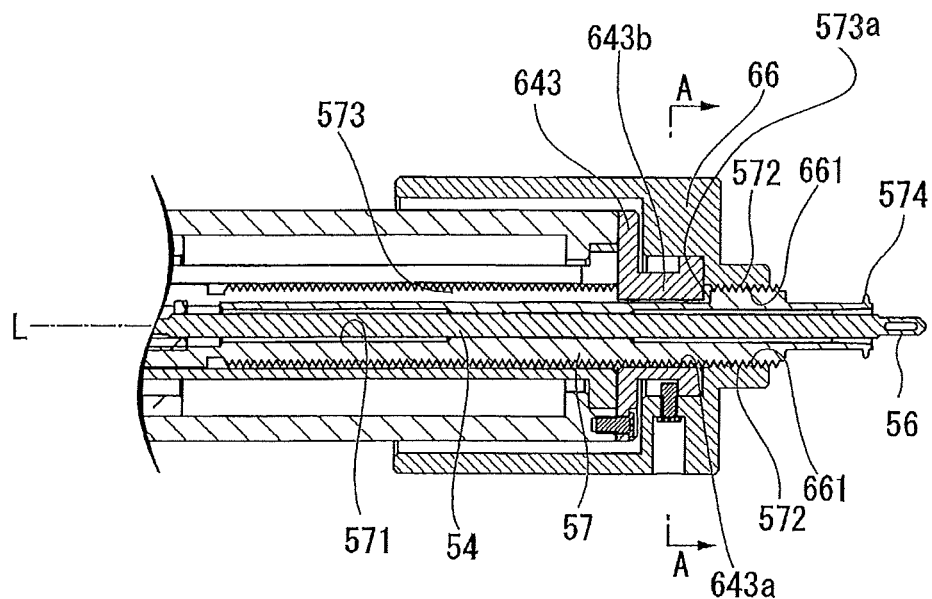
FIG. 6B is a cross-sectional view of a proximal end portion of the main manipulation part according to the embodiment of the present invention.
Figure 6C:
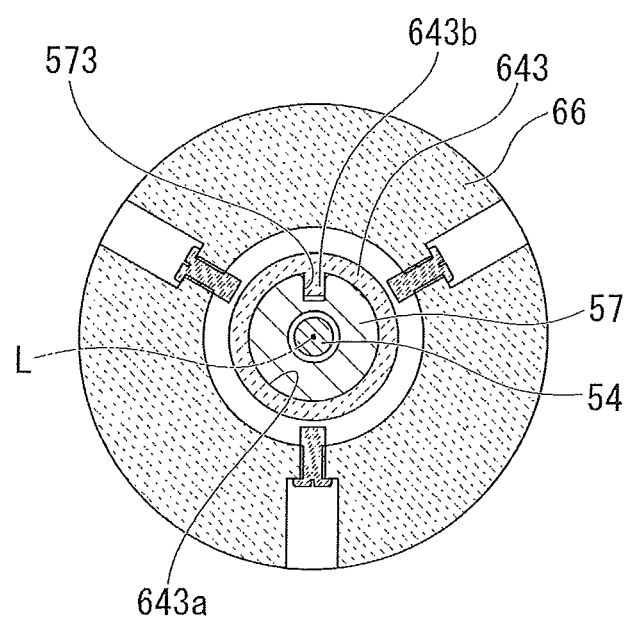
FIG. 6C is a cross-sectional view taken along line A-A in FIG. 6B.
Figure 8:
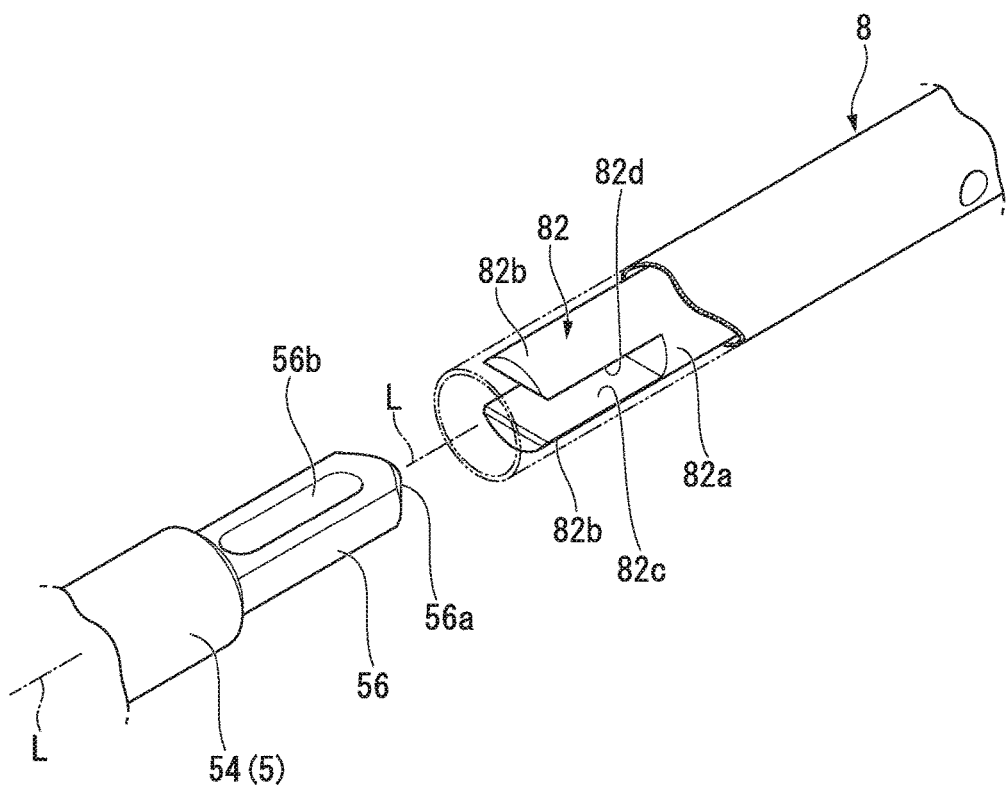
FIG. 8 is a perspective view of a proximal end portion of the stylet and a distal end portion of a manipulation transmission member according to the embodiment of the present invention.

As represented in FIGS. 6A, 6B, and 7, the stylet proximal end member 54 is inserted through a lumen 571 of a Luer joint (an intermediate member) 57. FIG. 8 is a perspective view of the proximal end portion (a stylet proximal end member) of the stylet 5 and a distal end portion of the transmission member 8. A proximal end engagement part 56 is provided on the stylet proximal end member 54. The proximal end engagement part 56 is an engagement member that engages with the distal end portion of the transmission member 8. As represented in FIG. 8, the proximal end engagement part 56 has a substantially flat plate shape and is provided to extend along the central axis L from a proximal end of the stylet proximal end member 54. A proximal end portion 56a of the proximal end engagement part 56 has a surface which protrudes toward a proximal end side. A through-hole 56b is formed in the proximal end engagement part 56. The proximal end engagement part 56 has a size such that the proximal end engagement part 56 is located inside a maximum outer diameter part of the stylet 5 when viewed from the direction of the central axis L.

As represented in FIG. 4, the stylet 5 and the needle tube 4 are inserted through the lumen 31 of the sheath 3 so as to be coaxial with the central axis L of the sheath 3. The sheath 3, the needle tube 4, and the stylet 5 are members that are inserted into a body from a distal end side, and are made of materials that are elastically deformable along with bending of the treatment tool channel 102 when inserted through the treatment tool channel 102 of the endoscope 100.

Figure 5:
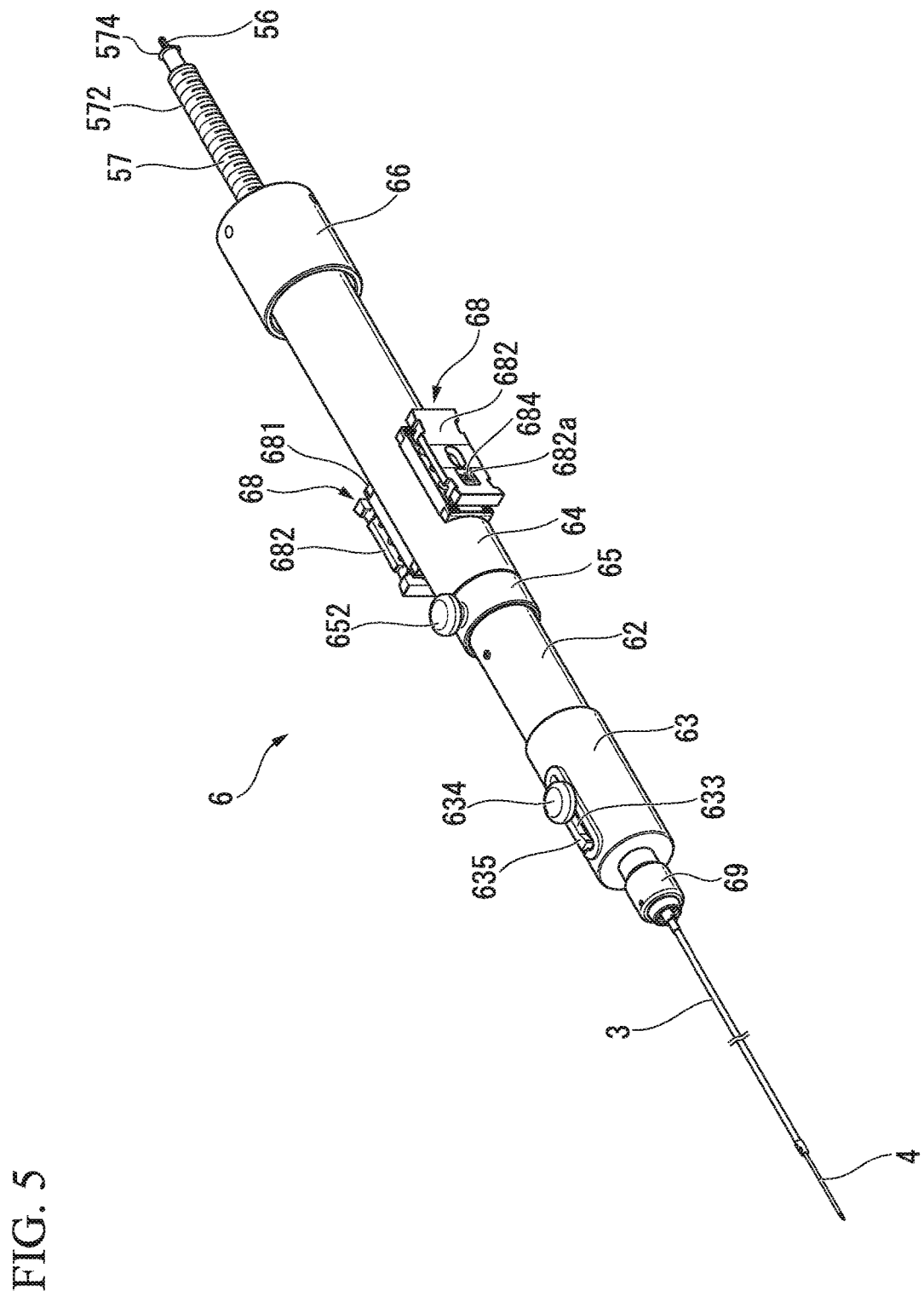
FIG. 5 is a perspective view of a main manipulation part according to the embodiment of the present invention.

The main manipulation part 6 is provided along the central axis L of the sheath 3 on the proximal end side of the sheath 3. FIG. 5 is a perspective view of the main manipulation part 6. FIG. 6A is a cross-sectional view of the main manipulation part 6. FIG. 6B is a cross-sectional view of a proximal end portion of the main manipulation part. FIG. 3 represents the main manipulation part 6 in a state in which a jig 9 to be described later is mounted thereon. FIGS. 5, 6A, 6B, and 6C illustrate the main manipulation part 6 from which the jig 9 is removed. The main manipulation part 6 is provided to operate the sheath 3, the needle tube 4, and the stylet 5. The main manipulation part 6 includes the first cam tube 61, a main manipulation part main body 62, a sheath slider 63, a needle slider (a slider unit and an elongated shaft manipulation part) 64, a needle slider stopper 65, a first rotation knob (an elongated shaft manipulation part and a first manipulation input part) 66, the needle guide (a guide member) 67, and a mounting part 69.

As represented in FIG. 7, the first cam tube 61 is a tube in which a first insertion passage 611 extending along the central axis L and a first guide passage (a cam, a guide passage, and a first helical groove) 612 are formed. The proximal end part of the stylet 5 is inserted through the first cum tube 61. The first guide passage 612 communicates with an inside and outside of a tube and is formed in a helical shape. The helical shape of the first guide passage 612 is formed such that the first engaging pin 55 advances from a proximal end of the first guide passage 612 to a distal end thereof while rotating right when viewed from the proximal end toward the distal end.

Figure 9:
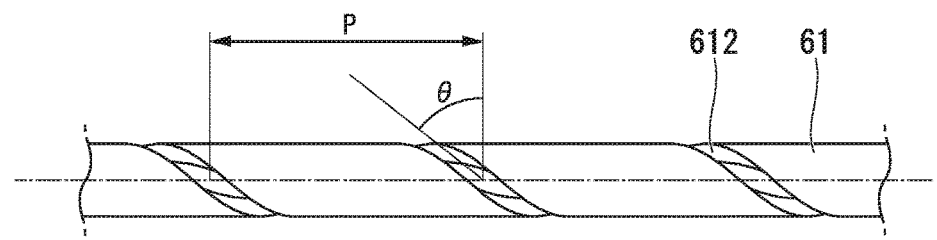
FIG. 9 is a schematic view representing a first guide passage of the first cam tube according to the embodiment of the present invention.

FIG. 9 is a schematic view representing the helical shape of the first guide passage 612. As represented in FIG. 9, the helical shape of the first guide passage 612 is formed at a constant pitch. A helical pitch P of the helical shape of the first guide passage 612 is formed at a pitch which is equal to a length obtained by dividing a length of the wire material of a coil in a part of the tissue-fastening tool 2 indwelled in a luminal organ on a proximal side by the number of turns of the coil of that part. Further, the number of turns of the helical shape of the first guide passage 612 is set to be greater than or equal to the number of turns of a partial coil that is indwelled in the luminal organ on the proximal side of the tissue-fastening tool 2. Furthermore, a lead angle θ of the first guide passage 612 is set within a range of 20 degrees or more to 75 degrees or less.

As represented in FIGS. 6A and 7, the stylet 5 and the stylet proximal end member 54 are inserted into the first cam tube 61. The first cam tube 61 and the three first engaging pins 55 of the stylet proximal end member 54 constitute a first helical mechanism 80. The first engaging pins 55 are slidably engaged in the first guide passage 612 of the first cam tube 61. The three first engaging pins 55 of the stylet proximal end member 54 are inserted into the first guide passage 612 to protrude outward from the first insertion passage 611. By the engagement between the three first engaging pins 55 and the first guide passage 612, the stylet 5 and the stylet proximal end member 54 are configured to be supported by the first cam tube 61 and to advance and retract while rotating with respect to the first cam tube 61. In this way, the helical mechanism defines the motion of the stylet 5.

A proximal end side of the first cam tube 61 and a distal end side of the Luer joint 57 are fixed to each other. The Luer joint 57 and the stylet 5 are configured to be relatively rotatable. The stylet 5 and the stylet proximal end member 54 can advance and retract in the direction of the central axis L while rotating with respect to the first cam tube 61 and the Luer joint 57.

Figure 6D:
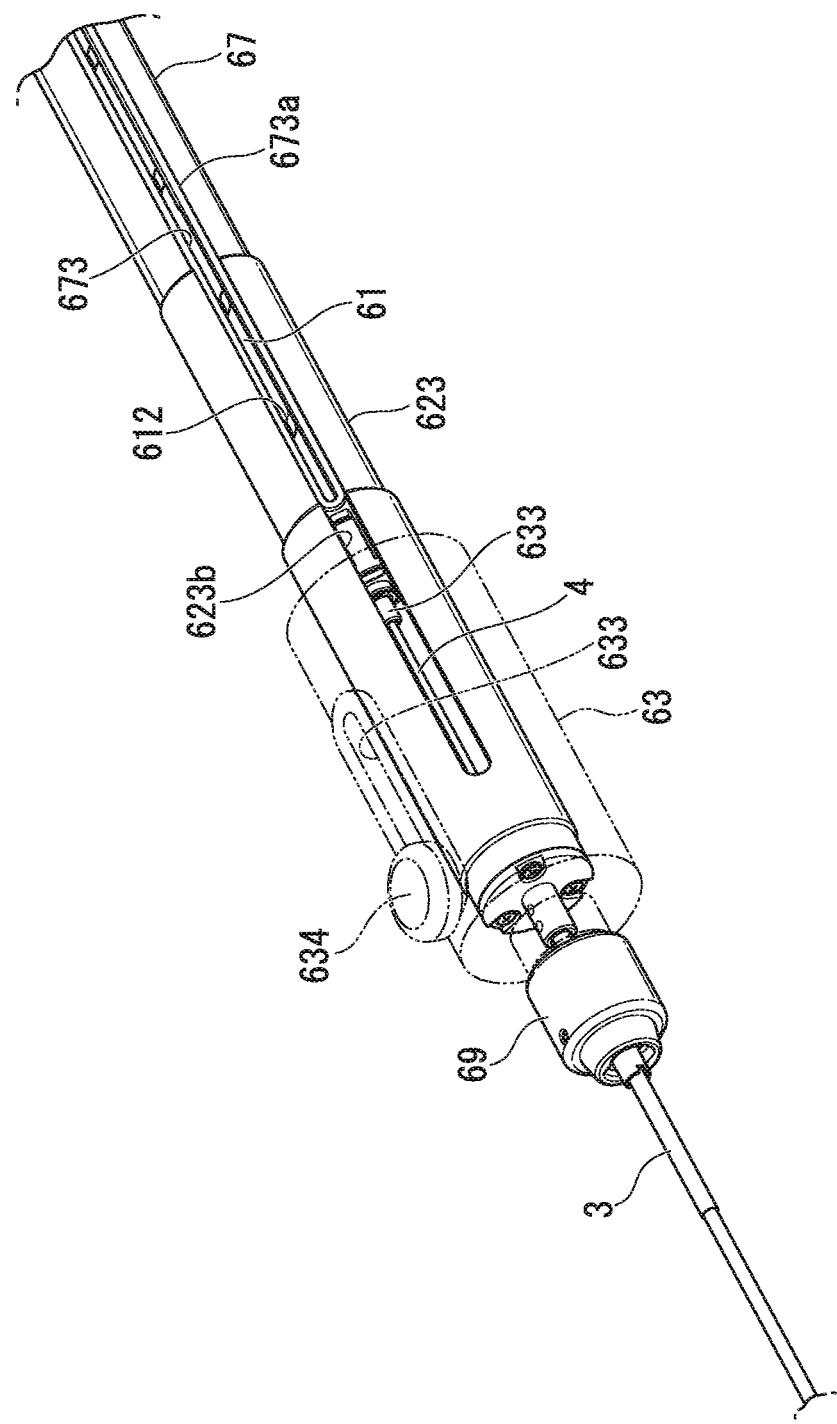
FIG. 6D is a perspective view representing a state in which a needle guide is inserted into a sheath guide according to the embodiment of the present invention.
Figure 10:
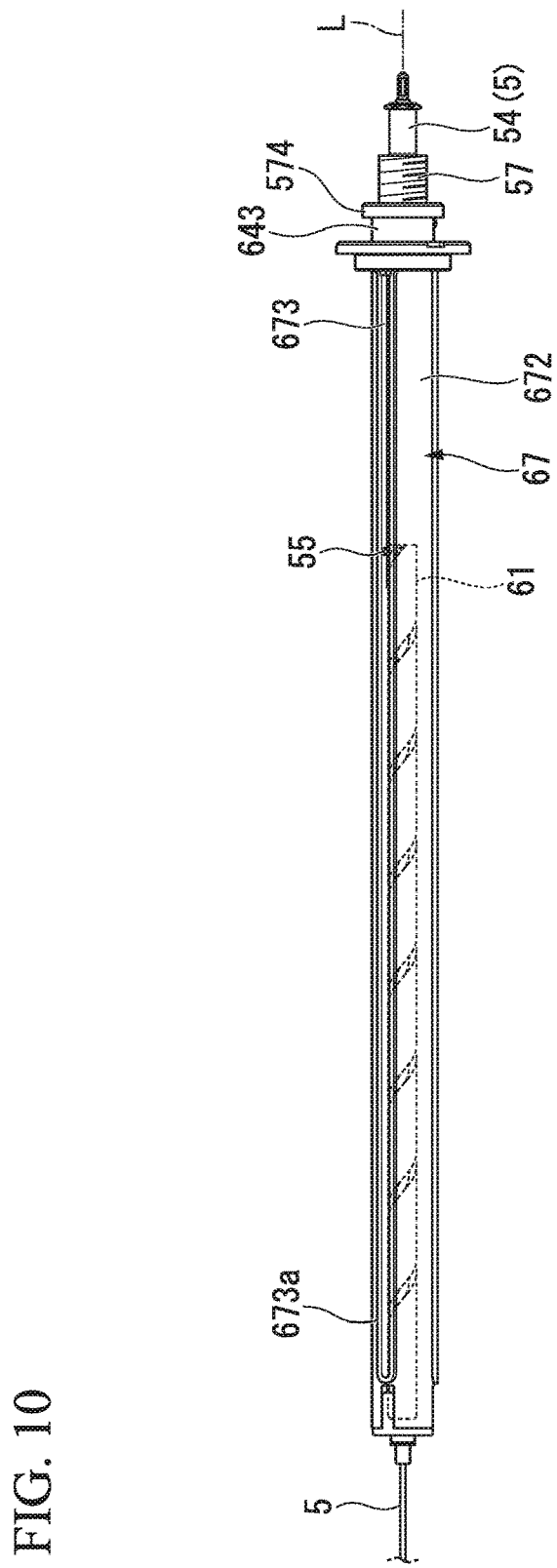
FIG. 10 is a side view representing a state in which the stylet and a stylet proximal end member are inserted into the needle guide according to the embodiment of the present invention.

As represented in FIG. 10, the needle guide 67 has a substantially cylindrical shape, and as represented in FIG. 6A, has a needle guide insertion passage 671 which extends in the direction of the central axis L. As represented in FIGS. 6D and 10, on a side wall part 672 of the needle guide 67, a slit surface that forms a guide slit 673 communicating an outside of the needle guide 67 and an inside of the needle guide insertion passage 671 is straightly formed along the direction of the central axis L. Three guide slits 673 are formed at equal intervals in a circumferential direction of the needle guide 67.

As represented in FIG. 6A, the needle guide insertion passage 671 is formed with a small-diameter part 671a having a small opening diameter of the needle guide insertion passage 671 in a partial region in the direction of the central axis L. The opening diameter of the small-diameter part 671a is set to be slightly larger than an outer diameter of the first cam tube 61.

The needle slider end member 643 is fixed to a proximal end of the needle slider 64. The needle guide 67 is sandwiched between the needle slider 64 and the needle slider end member 643 at a proximal end portion, and is supported to be capable of only rotating with respect to the needle slider 64.

The stylet 5, the stylet proximal end member 54, the first cam tube 61, and the Luer joint 57 are inserted into the needle guide insertion passage 671 to be advanceable and retractable with respect to the needle guide 67. When the first cam tube 61 is inserted through the small-diameter part 671a of the needle guide 67, the first cam tube 61 is supported to be relatively advanceable, retractable, and rotatable on the central axis L inside the needle guide insertion passage 671.

As represented in FIG. 10, the three first engaging pins 55 of the stylet proximal end member 54 are respectively engaged with the guide slits 673. The first engaging pin 55 is slidable inside the guide slit 673. That is, the first engaging pin 55 is slidable inside the first guide passage 612 and inside the guide slit 673.

The first cam tube 61 is supported to be capable of only advancing and retracting with respect to the needle slider 64. The first engaging pin 55 of the stylet proximal end member 54 is engaged with both the first guide passage 612 and the guide slit 673. When the stylet 5 and the stylet proximal end member 54 rotate around the central axis L, the stylet 5 and the stylet proximal end member 54 advance and retract with respect to the needle slider 64 while rotating, and the needle guide 67 is configured to only rotate with the stylet 5 and the stylet proximal end member 54. In this description, a motion in which the stylet 5 advances while rotating is referred to as a "helical motion" in some cases.

As represented in FIGS. 5 and 6A, the main manipulation part main body 62 has a substantially cylindrical shape, and a second insertion passage 621 extending in the direction of the central axis L is formed in the main manipulation part main body 62. A sheath guide 623 is inserted into a distal end side of the second insertion passage 621. The needle guide 67 is inserted into a proximal end side of the second insertion passage 621. The sheath guide 623 is rotatably supported with respect to the main manipulation part main body 62 near a distal end of the second insertion passage 621. A sheath fixing part 625 is fixed to a distal end portion of the sheath guide 623, and the proximal end of the sheath 3 is fixed to the sheath fixing part 625.

As represented in FIG. 6D, the sheath guide 623 is a substantially cylindrical member extending in the direction of the central axis L, and as represented in FIG. 6A, a third insertion passage 623a is formed therein. The stylet 5 inserted through the needle guide 67 and the first cam tube 61 is inserted through the third insertion passage 623a to be advanceable and retractable. In the sheath guide 623, first slits 623b straightly extending in the direction of the central axis L are formed at three positions at equal intervals in the circumferential direction. The first slits 623b are engaged with ribs 673a (see FIG. 10) formed on the radial outside of the circumference of the guide slit 673 of the needle guide 67. Therefore, when the needle guide 67 rotates around the central axis L, the sheath guide 623 rotates to follow the rotation. However, even if the needle guide 67 advances and retracts in the direction of the central axis L, the sheath guide 623 does not follow the movement. From the above, the first helical mechanism 80 rotates the sheath 3 around the central axis L due to the engagement between the cam and the cam follower.

The ring-shaped needle slider stopper 65 is externally mounted on the main manipulation part main body 62. The needle slider stopper 65 has an inner diameter that enables the needle slider stopper 65 to advance and retract in the direction of the central axis L with respect to the main manipulation part main body 62. A screw hole 651 is formed on the needle slider stopper 65. A needle stopper screw 652 is screwed into the screw hole 651. When the needle stopper screw 652 is inserted and screwed into the screw hole 651, a distal end of the needle stopper screw 652 presses an outer circumferential surface of the main manipulation part main body 62 and a position of the needle slider stopper 65 with respect to the main manipulation part main body 62 is fixed.

Figure 11:
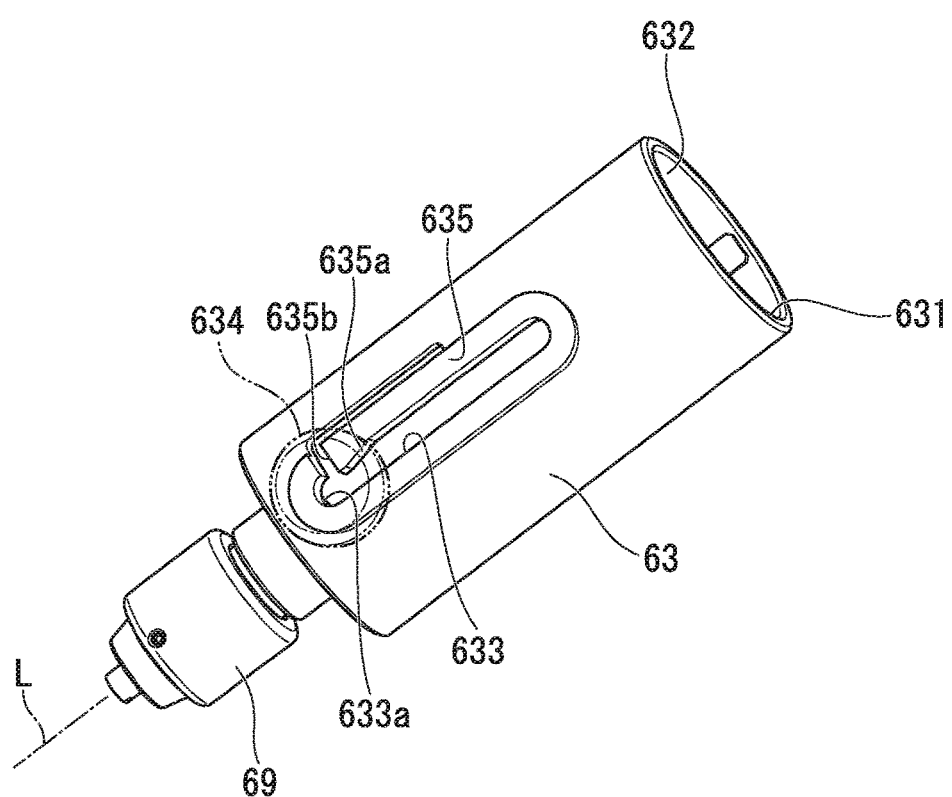
FIG. 11 is a perspective view of a sheath slider according to the embodiment of the present invention.

The sheath slider 63 is provided on a distal end side of the main manipulation part main body 62. As represented in FIGS. 5 and 11, the sheath slider 63 is a cylindrical member, and a fourth insertion passage 632 extending in the direction of the central axis L from a proximal end opening 631 is formed thereon. A distal end portion of the main manipulation part main body 62 is inserted into the proximal end opening 631. The main manipulation part main body 62 is provided to be advanceable and retractable inside the fourth insertion passage 632.

The mounting part 69 is fixed to a distal end of the sheath slider 63. The mounting part 69 is fixed to a manipulation part 104 of the endoscope 100 by being screw-engaged with a port 103 of the treatment tool channel 102 of the endoscope 100 (see FIG. 19). The main manipulation part 6 is fixed to the endoscope 100 by the mounting part 69. A distal end insertion passage 691 extending in the direction of the central axis L is formed in the mounting part 69. The sheath 3 is inserted through the distal end insertion passage 691 to be advanceable and retractable. The sheath 3 can be advanced and retracted by moving the main manipulation part main body 62 to advance and retract in a linear direction with respect to the sheath slider 63.

A second slit 633 extending in the direction of the central axis L is formed in the sheath slider 63. A fixing knob 634 is inserted into the second slit 633 from an outer circumference side thereof. A screw part 634a of the fixing knob 634 passes through the second slit 633 and protrudes toward a side of the fourth insertion passage 632 of the sheath slider 63. A distal end of the screw part 634a of the fixing knob 634 is inserted into a screw hole 623d formed on an outer periphery of the distal end portion of the main manipulation part main body 62. A length of the screw part 634a is set such that a screw head 634b of the fixing knob 634 can be slightly separated from the second slit 633 while maintaining a state in which a part of a distal end side of the screw part 634a is screwed into the screw hole of the main manipulation part main body 62.

When the screw part 634a is screwed into a side of the main manipulation part main body 62, the sheath slider 63 around the second slit 633 is clamped by the screw head 634b and the main manipulation part main body 62. As a result, a positional relationship between the sheath slider 63 and the main manipulation part main body 62 in the direction of the central axis L is fixed. When screwing of the screw part 634a is loosened, the main manipulation part main body 62 is in a state that is capable of advancing and retracting in the linear direction with respect to the sheath slider 63. That is, relative positions of the main manipulation part main body 62 to the sheath slider 63 can be switched into a fixed state or a relatively movable state due to the second slit 633 and the fixing knob 634.

Depending on a position of the fixing knob 634 with respect to the second slit 633, an amount of protrusion of the sheath 3 from the main manipulation part 6 (an amount of protrusion from the mounting part 69) is determined. A length of the second slit 633 in the direction of the central axis L corresponds to an advancement and retraction movement length of the sheath 3. When the fixing knob 634 is disposed at a position at which the fixing knob 634 comes into contact with a distal end of the second slit 633, the amount of protrusion of the sheath 3 from a distal end of the main manipulation part 6 (the amount of protrusion from the mounting part 69) is maximized. Meanwhile, when the fixing knob 634 is disposed at a position at which it comes into contact with a proximal end of the second slit 633, the sheath 3 is disposed at a maximally retracted position, and the amount of protrusion of the sheath 3 from the distal end of the main manipulation part 6 is minimized As represented in FIGS. 5 and 11, a resin spring 635 configured of a cantilever extending in the direction of the central axis L is provided in a part of the second slit 633 of the sheath slider 63. As represented in FIG. 11, the resin spring 635 is provided with an inclined surface 635a and a locking surface 635b. When the fixing knob 634 is advanced to a distal side in the direction of the central axis L, the screw part 634a comes in contact with the inclined surface 635a and advances while gradually pressing the resin spring 635, and comes into contact with the distal end 633a of the second slit 633. The screw part 634a is disengaged from the inclined surface 635a when coming into contact with the distal end 633a of the second slit 633, and the resin spring 635 returns to an original position thereof. Even if a force returning the fixing knob 634 to a proximal end side in the direction of the central axis L acts in this state, the screw part 634a does not return because the screw part 634a comes into contact with the locking surface 635b. As described above, even if the screw part 634a is not screwed into the main manipulation part main body 62, the sheath slider 63 can be fixed while the amount of protrusion of the sheath 3 from the main manipulation part 6 is maximized As represented in FIGS. 5 and 6A, the needle slider 64 has a substantially cylindrical shape and is provided along the central axis L in an intermediate part of the main manipulation part 6 in the direction of the central axis L. In a fifth insertion passage 641 formed in the needle slider 64, the stylet 5, the first cam tube 61, the needle guide 67, and the main manipulation part main body 62 are sequentially coaxially disposed from a side of the central axis L toward the outside in the radial direction. The first rotation knob 66 (the rotation knob), which will be described later, is disposed at a proximal end portion of the needle slider 64.

Figure 12A:
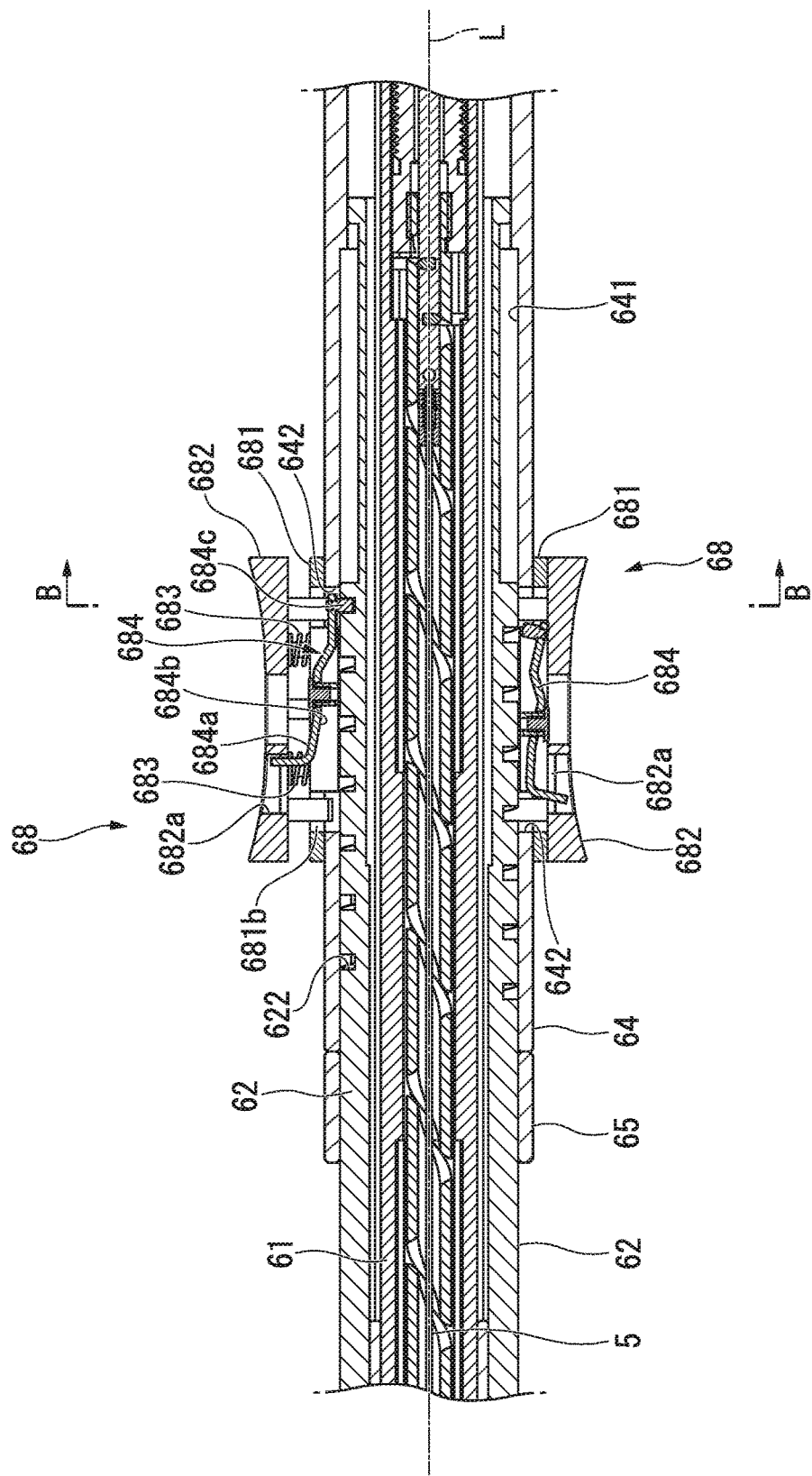
FIG. 12A is a partial cross-sectional view of the main manipulation part according to the embodiment of the present invention.

As represented in FIG. 12A, a pair of side holes 642 are formed in the needle slider 64 at a position where are opposed to an outer circumference in the radial direction. As represented in FIGS. 5 and 12A, a slide button unit 68 is provided in each of the pair of side holes 642. The slide button unit 68 is provided to switch between a state in which the needle slider 64 can advance and retract in the direction of the central axis L with respect to the main manipulation part main body 62 and a state in which the needle slider 64 can advance and retract while rotating around the central axis L. The lower side of FIG. 12A represents the slide button unit 68 in a state in which the needle slider 64 can advance and retract in the direction of the central axis L with respect to the main manipulation part main body 62, and the upper side of FIG. 12A represents the slide button unit 68 in a state in which the needle slider 64 can advance and retract while rotating around the central axis L with respect to the main manipulation part main body 62. Actually, the pair of slide button units 68 is switched to one of a state represented on the upper side of FIG. 12A or a state represented on the lower side of FIG. 12.

A base body 681 of the slide button unit 68 is fitted into the side hole 642 and fixed to the needle slider 64, and a button main body 682 is attached to an outer surface 681a of the base body 681 in a radial direction. A spring member 683 is provided as a biasing member between the button main body 682 and the base body 681. The button main body 682 is biased in a direction away from the base body 681 toward the outer side in the radial direction by the spring member 683.

The slide button unit 68 further includes a plate 684 between the button main body 682 and the base body 681. The plate 684 is disposed to extend in the direction of the central axis L, and a substantially intermediate part of the plate 684 in the direction of the central axis L is fixed to the base body 681. A hole 681b formed along the central axis L is formed in the base body 681. A distal end portion of the plate 684 is engaged with the slit 682a of the button main body 682, and a proximal end portion of the plate 684 is disposed in the hole 681b of the base body 681. A first surface 684a of the plate 684 faces the button main body 682, and a second surface 684b is located in the hole 681b and disposed to face the main manipulation part main body 62. A locking pin (the locking part) 684c is provided at the proximal end portion of the plate 684 to protrude from the second surface 684b in a thickness direction (an inward in a radial direction of the base body 681) of the plate 684. A helical groove (the second helical groove) 622 is formed on an outer circumferential surface of an intermediate region of the main manipulation part main body 62 in the direction of the central axis L, and the locking pin 684c is switched between a state of being engaged with the helical groove 622 and a state of not being engaged with the helical groove 622 as represented in FIG. 12A.

Figure 12B:
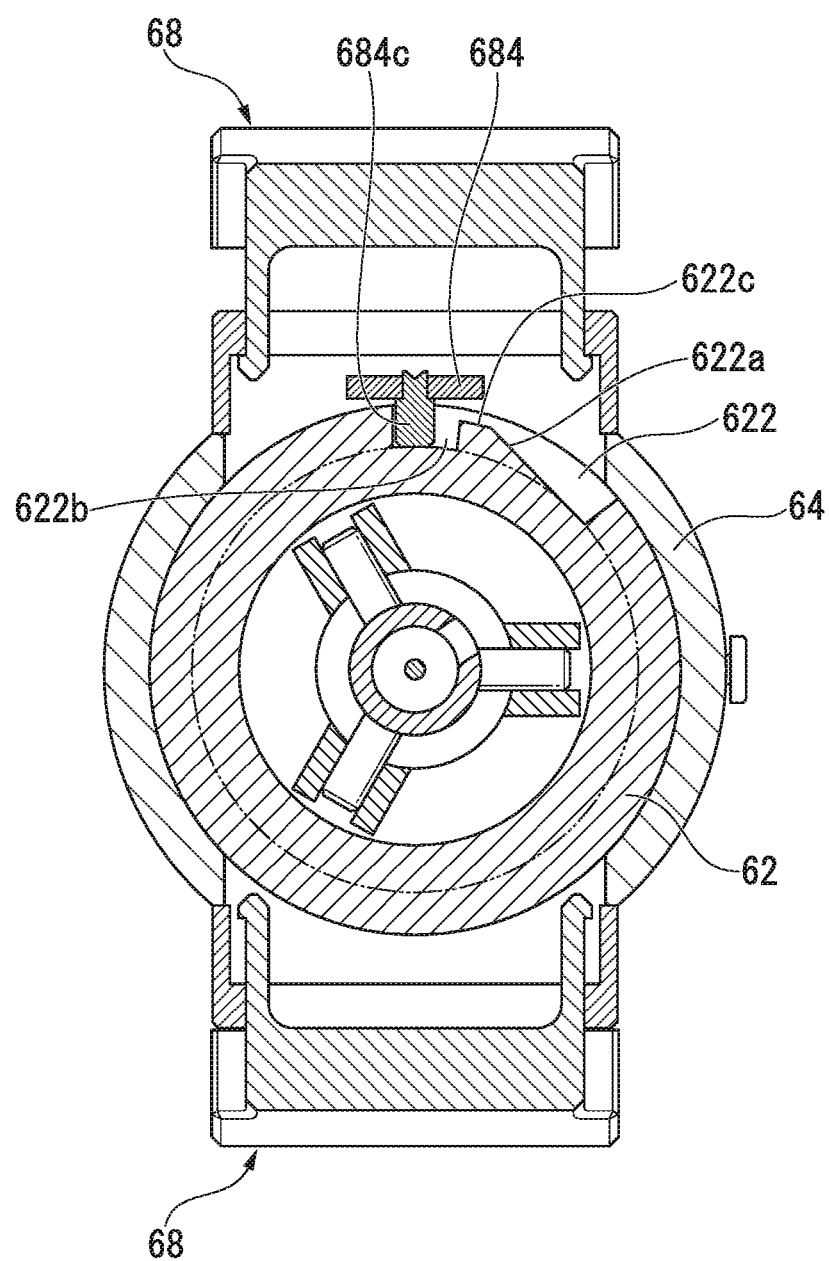
FIG. 12B is a cross-sectional view taken along line B-B in FIG. 12A.

FIG. 12B is a cross-sectional view of the main manipulation part main body 62 taken along line B-B of FIG. 12A. As represented in FIG. 12B, a step defined by an oblique portion 622a and a dent portion 622b that are adjacent to each other is formed at a proximal end portion of the helical groove 622. To be specific, the dent portion 622b is formed at the proximal end of the helical groove 622, and the oblique portion 622a is continuous with the dent portion 622b and is formed at a distal side of the helical groove 622 than the dent portion 622b. The oblique portion 622a is curvilinearly or linearly formed such that a groove depth of the helical groove 622 is gradually reduced toward the dent portion 622b and has a shallowest groove (a shallowest groove portion 622c) that is continuous with the dent portion 622b. On the other hand, the dent portion 622b is dented such that the groove depth is sharply increased at a boundary with the shallowest groove portion 622c. That is, an inner wall surface of the dent portion 622b has a greater inclined angle than the oblique portion 622a at the boundary with the shallowest groove portion 622c in a helical direction following the helical groove 622. The dent portion 622b, the oblique portion 622a, and the locking pin 684c constitute a needle anti-movement mechanism. The needle anti-movement mechanism is configured to prevent movement of the locking pin 684c by the dent portion 622b and the oblique portion 622a. When an operator moves the needle slider 64 to the extreme proximal end side while rotating the needle slider 64, the locking pin 684c passes over the aforementioned oblique portion 622a and is fitted into the dent portion 622b by the needle anti-movement mechanism, and the locking pin 684c located at the dent portion 622b is put in a state in which it cannot move.

When the button main body 682 is pressed inward in the radial direction by the operator and is pushed in until the button main body 682 comes into contact with the base body 681, the distal end portion of the plate 684 is pressed toward the main manipulation part main body 62 side. Accordingly, the proximal end portion of the plate 684 moves away from the main manipulation part main body 62, and the locking pin 684c is detached from the helical groove 622. In this state, since a connection relationship between the needle slider 64 and the main manipulation part main body 62 is released, a movement of the needle slider 64 is not restricted by the helical groove 622, and the needle slider 64 is configured to be advanceable and retractable in the direction of the central axis L with respect to the main manipulation part main body 62.

It is not necessary to push the button main body 682 in until the button main body 682 comes into contact with the base body 681. For example, the fitting of the locking pin 684c may be capable of releasing before contacting the button main body 682 with the base body 681.

In a state in which the button main body 682 is biased by the spring member 683 outward in the radial direction and is separated from the base body 681, the distal end portion of the plate 684 is pulled by the button main body 682 outward in the radial direction, and the proximal end portion of the plate 684 is biased toward the main manipulation part main body 62 side. At this point, the locking pin 684c is fitted into the helical groove 622 formed in the outer circumferential surface of the main manipulation part main body 62. In this state, the needle slider 64 is configured to be advanceable and retractable with respect to the main manipulation part main body 62 while rotating along the helical groove 622.

The locking pin 684c is capable of being moved to the proximal end of the helical groove 622 when an operator manipulates the slider 64 in a state in which the locking pin 684c is fitted into the helical groove 622. Therefore, the locking pin 684c passes over the oblique portion 622a and is fitted into the dent portion 622b in accordance with a manipulation of the needle slider 64 by the operator. In s state in which the locking pin 684c is fitted into the dent portion 622b, the locking pin 684c is biased toward the main manipulation part main body 62 side by the spring member 683. For this reason, as long as the locking pin 684c does not pass over the shallowest groove portion 622c of the oblique portion 622a, the needle slider 64 is not capable of being advanced while rotating along the helical groove 622. That is, the locking pin 684c is locked in the helical direction of the helical groove 622, and the movement of the needle slider 64 with respect to the main manipulation part main body 62 is prevented. In this state, as long as the button main body 682 is again pressed inward in the radial direction by the operator and is not pushed in until the button main body 682 comes into contact with the base body 681, the fitting of the locking pin 684c into the dent portion 622b cannot be intentionally released, and the needle slider 64 is put in a state in which the needle slider 64 is not capable of being advanced.

The first rotation knob 66 is a member that is rotationally manipulated by the operator when sending the tissue-fastening tool 2 from the distal end of the needle tube 4. As represented in FIGS. 5, 6A, 6B, and 6C, the first rotation knob 66 is a cylindrical member and is attached to cover a side surface and a proximal end side of the needle slider end member 643. The first rotation knob 66 is rotatably attached to the needle slider end member 643. A female screw 661 is formed at the center of the first rotation knob 66, and is engaged with a male screw 572 which is cut around an outer periphery of the Luer joint 57. An engaging projection 643b that protrudes in the radial direction is formed in a through-hole 643a which is a substantial center of the needle slider end member 643. A linear groove 573 extending in the direction of the central axis L is formed on the outer periphery of the Luer joint 57. The engaging projection 643b is engaged with the linear groove 573. With this configuration, the Luer joint 57 and the first cam tube 61 fixed to the Luer joint 57 are advanced straight with respect to the first rotation knob 66 by the first rotation knob 66 being rotated.

At the same time, the stylet 5 engaged with the first cam tube 61 is advanced straight with respect to the first rotation knob 66.

Figure 13:
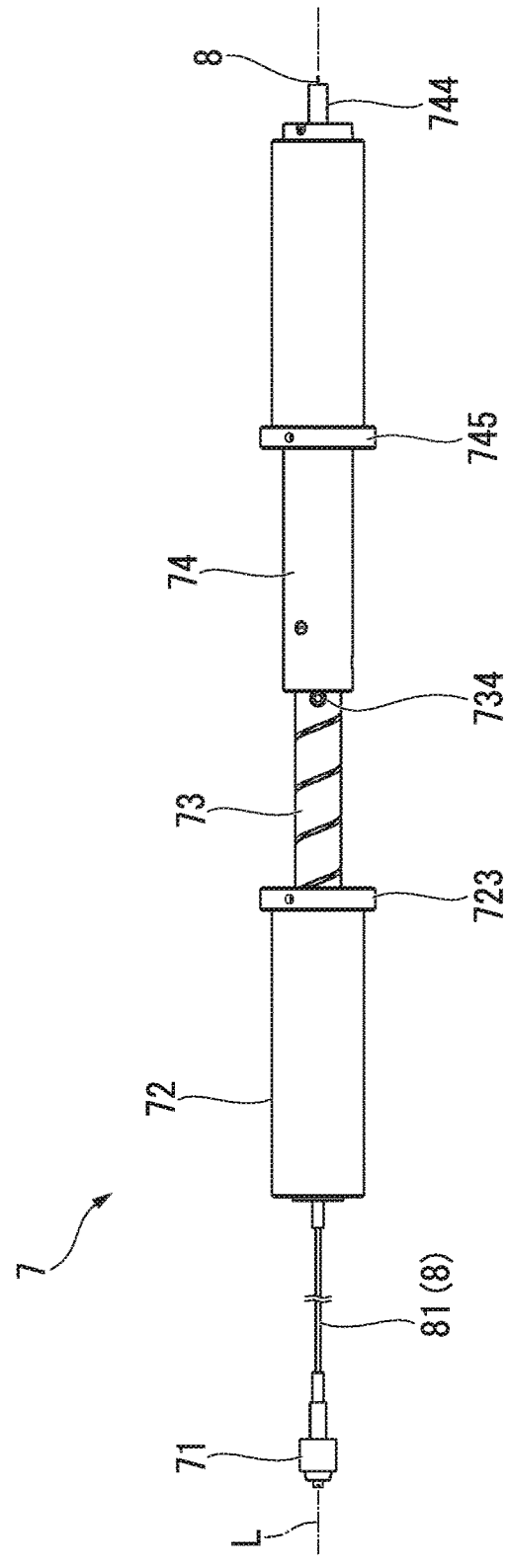
FIG. 13 is a side view of an auxiliary manipulation part according to the embodiment of the present invention.

FIG. 13 is a side view of the auxiliary manipulation part 7 when viewed from a direction orthogonal to the central axis L. The auxiliary manipulation part 7 is disposed to be separated from the main manipulation part 6 and is connected to the main manipulation part 6 via the transmission member 8. The main manipulation part 6 and the auxiliary manipulation part 7 are configured to be separably connected via the transmission member 8. The auxiliary manipulation part 7 advances and retracts the transmission member 8 to manipulate the movement of the stylet 5 within the main manipulation part 6. The auxiliary manipulation part 7 includes a manipulation coupling part 71, an auxiliary manipulation part main body 72, a second cam tube 73, and a rotation handle (the second manipulation input part) 74 in order from a distal end side thereof, and the transmission member 8 is inserted throughout the entire length in the direction of the central axis L.

Figure 14A:
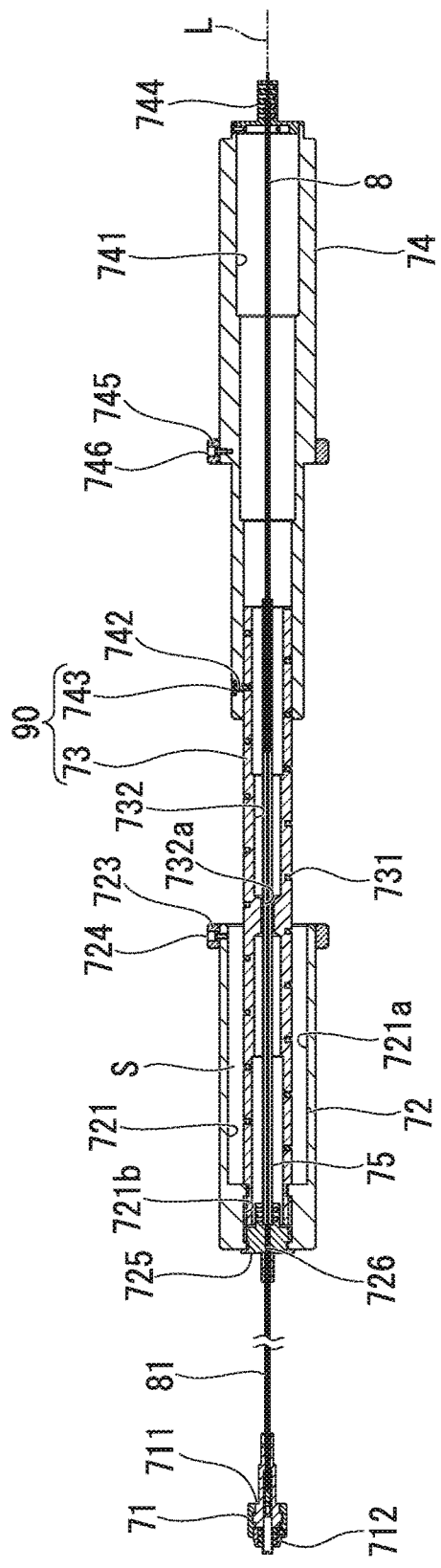
FIG. 14A is a cross-sectional view of the auxiliary manipulation part according to the embodiment of the present invention.
Figure 14B:
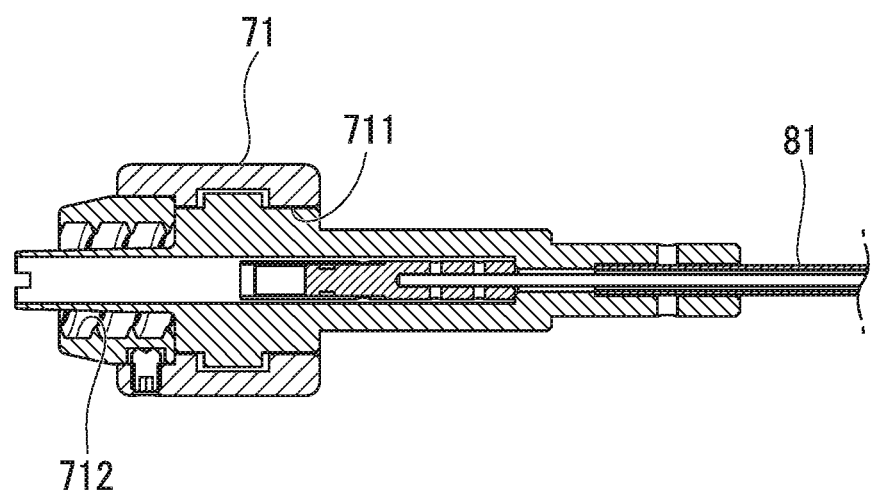
FIG. 14B is a cross-sectional view of a manipulation connection part according to the embodiment of the present invention.

FIG. 14A is a cross-sectional view of the auxiliary manipulation part 7 in a plane passing through the central axis L. FIG. 14B is a cross-sectional view of the manipulation coupling part 71. The manipulation coupling part 71 is a member that is connected to the proximal end portion of the main manipulation part 6 and couples the proximal end portion of the stylet 5 and the distal end portion of the transmission member 8. A sixth insertion passage 711 extending in the direction of the central axis L is formed in the manipulation coupling part 71. A screw groove 712 capable of being screwed to a flange 574 of the Luer joint 57 (see FIG. 5) is formed around the central axis L on an inner circumferential surface of a distal end portion of the sixth insertion passage 711.

The transmission member 8 is a long and flexible core material (a flexible member). A distal end side from a substantially central part of the transmission member 8 in the direction of the central axis L is inserted into a cable tube 81 having flexibility. The transmission member 8 is a transmission member that transmits a manipulation input of the auxiliary manipulation part 7 on the rotation handle 74 to the main manipulation part 6.

As represented in FIG. 8, a stylet engagement part 82 is provided at the distal end of the transmission member 8. The stylet engagement part 82 has two arms 82b extending in parallel with the direction of the central axis L from a base part 82a having a substantially columnar outer shape. The two arms 82b have planar parts 82c and 82d that face each other across the central axis L. A separation distance between the planar parts 82c and 82d in the radial direction (a direction orthogonal to the central axis L) is set to be slightly larger than a plate thickness of the proximal end engagement part 56 of the main manipulation part 6.

The transmission member 8 is inserted into the sixth insertion passage 711 to be advanceable, retractable, and rotatable with respect to the manipulation coupling part 71. In a state in which the auxiliary manipulation part 7 is not coupled to the main manipulation part 6, the distal end of the transmission member 8 is disposed at a substantially intermediate part of the sixth insertion passage 711 in the direction of the central axis L.

The stylet engagement part 82 is configured so that the stylet 5 and the transmission member 8 are engaged with each other when the proximal end engagement part 56 is inserted between the two arms 82b on the central axis L. When the stylet 5 and the transmission member 8 are engaged with each other, the planar parts 82c and 82d come into contact with the proximal end engagement part 56, and the rotational motion of the transmission member 8 can be transmitted to the stylet 5. Further, the stylet 5 can advance when the transmission member 8 advances.

The auxiliary manipulation part main body 72 has a tubular shape and is disposed on a distal end side of the auxiliary manipulation part 7. As represented in FIG. 14A, a seventh insertion passage 721 extending in the direction of the central axis L is formed in the auxiliary manipulation part main body 72. The seventh insertion passage 721 includes a first region 721a on a proximal end side thereof, and a second region 721b which is located on a distal end side from the first region 721a and has an opening diameter smaller than an opening diameter of the first region 721a. A first ring member 723 is externally fixed to an outer circumferential surface of a proximal end portion of the auxiliary manipulation part main body 72 and is fixed by a screw 724.

A connector 725 is fixed to a distal end portion of the auxiliary manipulation part main body 72. Specifically, the connector 725 is inserted to block a distal end opening of the second region 721b of the seventh insertion passage 721 and is fixed to the auxiliary manipulation part main body 72. An eighth insertion passage 726 is formed in the connector 725 along the central axis L, and a distal end portion of a guide tube 75 to be described later is fixed to a proximal end side of the eighth insertion passage 726. The cable tube 81 is fixed to a distal end side of the eighth insertion passage 726. The transmission member 8 is inserted into the guide tube 75 and the cable tube 81 fixed in the eighth insertion passage 726 and extends to the manipulation coupling part 71.

Figure 15:
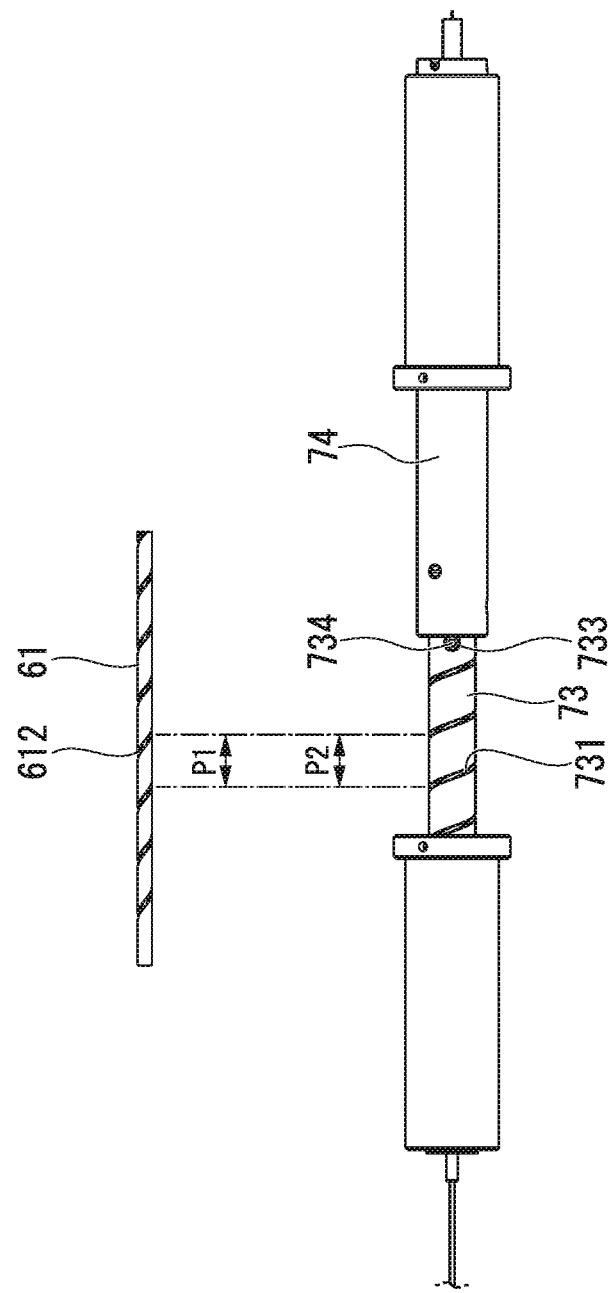
FIG. 15 is a diagram representing a relationship between the first guide passage and a second guide passage according to the embodiment of the present invention.

The second cam tube 73 is a long tubular member, and a second guide passage (a fourth helical groove) 731 configured of a groove formed around the central axis L in a helical shape and distal and proximal end portions of the second guide passage 731 are formed on an outer circumferential surface of the second cam tube 73. As represented in FIG. 15, the second guide passage 731 of the second cam tube 73 and the first guide passage 612 of the first cam tube 61 are formed at the same helical pitches P1 and P2 and in the same rotational direction. A distal end side of the second cam tube 73 is inserted through the first region 721a of the seventh insertion passage 721 of the auxiliary manipulation part main body 72, and a distal end portion of the second cam tube 73 is fixed to the second region 721b. As represented in FIG. 15, the second cam tube 73 has a fitting hole 733 at a region in the outer circumferential surface of the second cam tube 73 between the grooves of the second guide passage 731. The fitting hole 733 is a hole formed through a wall surface of the second cam tube 73 for a rod-like member 734 such as a split pin or a screw to be fitted therein. The fitting hole 733 is formed to be exposed at a position where is more distal side of the second cam tube 73 than the distal end of the rotation handle 74 when the rotation handle 74 is moved to the extreme proximal side, that is, when a second engaging pin 743 (to be described below) comes into contact with an end of the second guide passage 731 of the second cam tube 73. For this reason, as represented in FIG. 13, in the state in which the rotation handle 74 (to be described below) is moved to the extreme proximal side, the rotation handle 74 cannot be moved forward due to the rod-like member 734 such as a split pin or a screw inserted into the fitting hole 733.

As represented in FIG. 14A, a gap S is formed between an inner circumferential surface of the first region 721a and an outer circumferential surface of the second cam tube 73. The second cam tube 73 has a cam insertion passage 732 extending in the direction of the central axis L. The cam insertion passage 732 is formed with a reduced diameter part 732a in which an opening diameter is reduced in a substantially central part in the direction of the central axis L.

The guide tube 75 having a length substantially equal to that of the second cam tube 73 is inserted into the cam insertion passage 732. A distal end portion of the guide tube 75 is fixed to the eighth insertion passage 726 of the connector 725 as described above. Since a proximal end side of the guide tube 75 is inserted through the reduced diameter part 732a of the cam insertion passage 732, the guide tube 75 is arranged so that a center thereof coincides with the central axis L. The transmission member 8 is inserted in the guide tube 75 to be advanceable and retractable. With this configuration, the transmission member 8 is supported on the central axis L to be advanceable and retractable within the auxiliary manipulation part 7.

As represented in FIGS. 13 and 14A, the rotation handle 74 is a tubular member, and is disposed at a proximal end portion of the auxiliary manipulation part 7. A ninth insertion passage 741 extending in the direction of the central axis L is formed in the rotation handle 74 and the ninth insertion passage 741 has an inner surface. An opening diameter of a distal end side region of the ninth insertion passage 741 is set to be slightly larger than an outer diameter of the second cam tube 73. Three screw holes 742 communicating an outer circumferential surface and the inside of the ninth insertion passage 741 are formed at a distal end portion of the rotation handle 74 (two screw holes 742 are not represented in FIG. 14A). Each of the screw holes 742 is provided at the same interval in the circumferential direction at every ⅓ turn (an angle of 120 degrees) and is provided at the same interval in the longitudinal direction at every ⅓ length of the aforementioned helical pitch.

The second cam tube 73 is inserted into the ninth insertion passage 741. In the state in which the second cam tube 73 is inserted into the ninth insertion passage 741 of the rotation handle 74, the second engaging pin (the second engaging part) 743 is screwed and fixed to each of the screw holes 742. Each of the second engaging pin 743 protrudes from the inner surface of the rotation handle 74 and those protrudes into the ninth insertion passage 741, and a distal end portion thereof is slidably engaged with the inside of the second guide passage 731. An outer diameter of a distal end portion of the second engaging pin 743 is smaller than an opening width of the second guide passage 731. Therefore, the distal end portion of the second engaging pin 743 is configured to be relatively movable inside the second guide passage 731 in accordance with the rotation of the rotation handle 74. The second cam tube 73 and the second engaging pin 743 constitute a second helical mechanism 90.

A fixing member 744 that covers a proximal end opening of the ninth insertion passage 741 is fixed to a proximal end portion of the rotation handle 74. The proximal end portion of the transmission member 8 and the proximal end portion of the rotation handle 74 are fixed to each other by the fixing member 744. Therefore, the proximal end portion of the transmission member 8 follows the manipulation of the rotation handle 74. That is, the second helical mechanism 90 advances the transmission member 8 while rotating the transmission member 8 with respect to the auxiliary manipulation part main body 72.

A second ring member 745 is externally fixed to an outer circumferential surface of a substantially central part of the rotation handle 74 in the direction of the central axis L and is fixed by a screw 746. An outer diameter of the rotation handle 74 on a position closer to a distal side than the second ring member 745 is set to be slightly smaller than the opening diameter of the first region 721a of the seventh insertion passage 721.

In the indwelling device 1 having the aforementioned configuration, the main manipulation part 6 can perform various manipulations such as advancement, retraction, and rotation of the sheath 3, advancement and retraction of the needle tube 4, and advancement, retraction, and rotation of the stylet 5. The auxiliary manipulation part 7 is configured such that advancement, retraction, and rotational manipulation of the transmission member 8 can be performed and manipulation on the needle tube 4 may not be performed.

Figure 16:
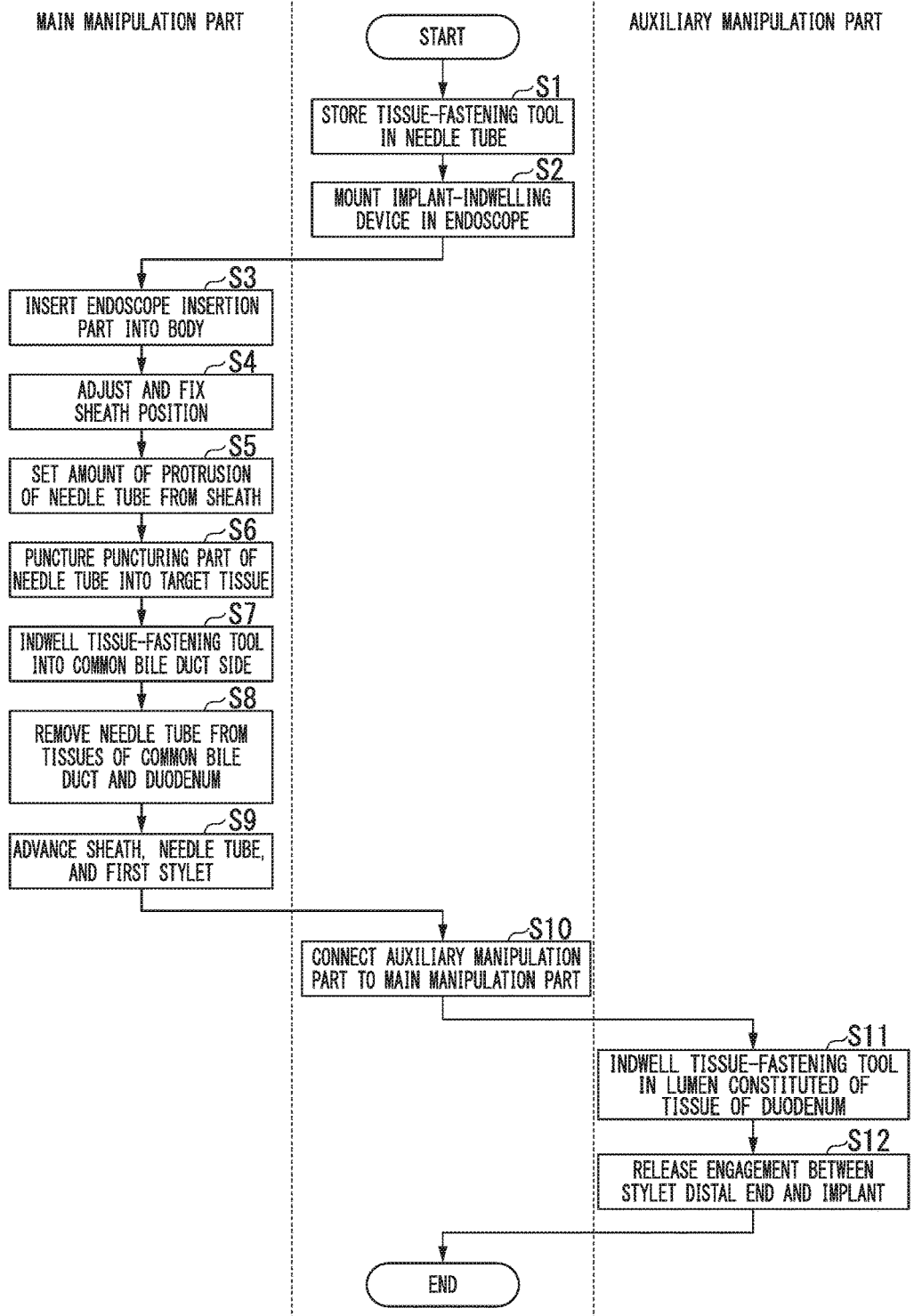
FIG. 16 is a flowchart of a procedure in which the tissue-fastening tool indwelling device according to the embodiment of the present invention is used.

Next, regarding the motion of the indwelling device 1, an example of a procedure of mounting the indwelling device 1 to an ultrasonic endoscope (hereinafter referred to as an "endoscope") and indwelling the tissue-fastening tool 2 to penetrate the tissue D of a duodenum and the tissue CBD of a common bile duct will be described. FIG. 16 is a flowchart representing the procedure of this embodiment.

The indwelling device 1 is configured such that a motion (a first motion) of the stylet 5 that moves from the proximal side to the distal side with respect to the needle tube 4 is capable of being manipulated by both of the main manipulation part 6 and the auxiliary manipulation part 7. The stylet 5 has a first state in which the stylet 5 is advanced straight with respect to the needle tube 4 and the sheath until the entirety from a distal end 27 to a proximal end of the distal end side region 25 of the tissue-fastening tool 2 protrudes from the needle tube 4. Further, the stylet 5 has a second state in which the stylet 5 is advanced while being rotated until the entirety from a distal end to a proximal end of the proximal end side region 26 of the tissue-fastening tool 2 protrudes from the needle tube 4. A maximum movable amount of the stylet 5 in the first state in a direction along the longitudinal axis of the sheath 3 due to the manipulation of the main manipulation part 6 (the first rotation knob 66) may be set to be smaller than a maximum movable amount of the stylet 5 in the second state in a direction along the longitudinal axis of the sheath 3 due to the manipulation of the auxiliary manipulation part 7 (the rotation handle 74). In addition, the indwelling device 1 is configured such that manipulation (a second motion) of the needle tube 4 is performed only by the main manipulation part 6. This will be described in detail below.

Figure 17:
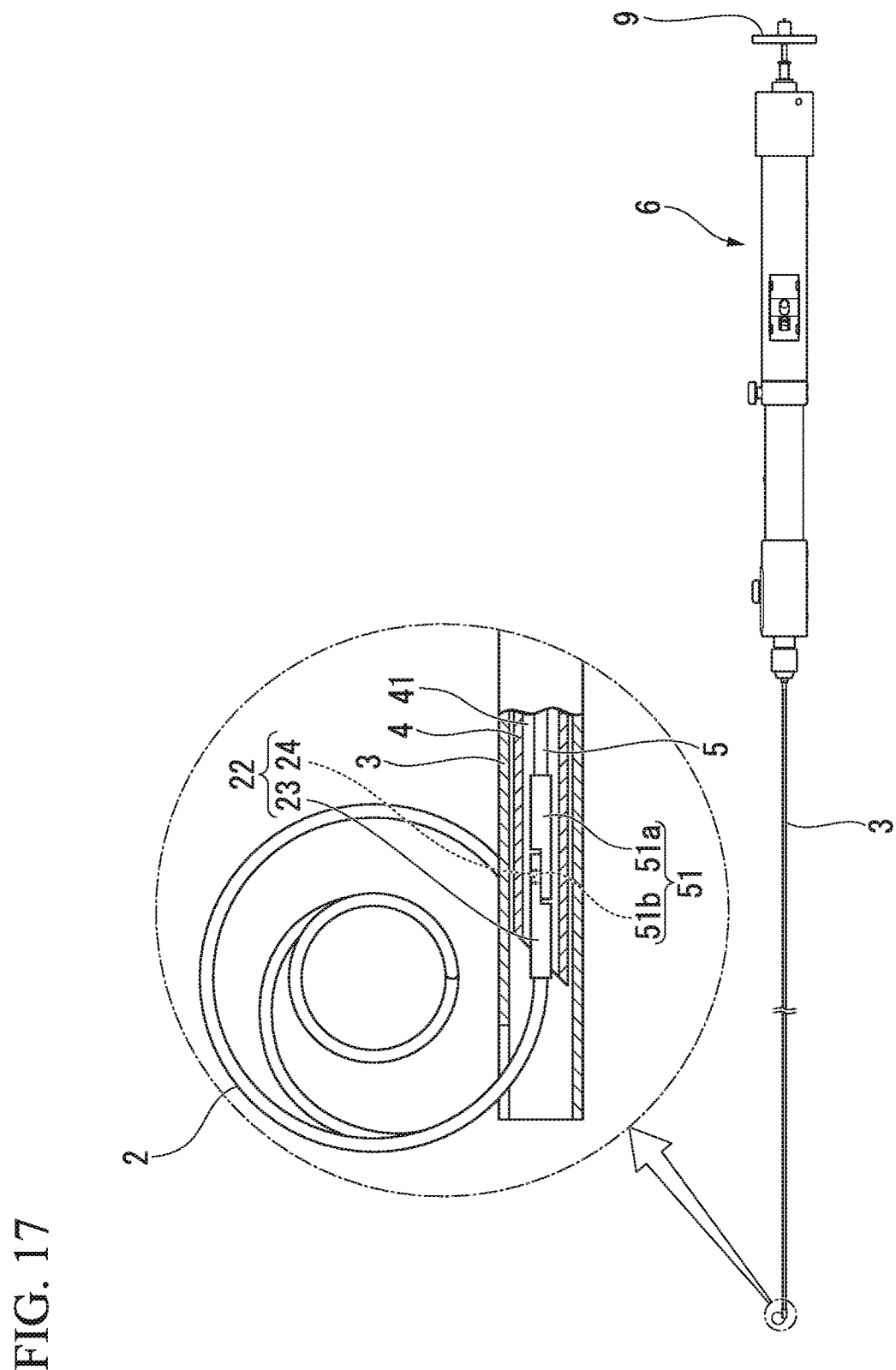
FIG. 17 is a side view representing an initial state of the main manipulation part according to the embodiment of the present invention.

FIG. 17 is a side view representing an initial state of the main manipulation part 6. As represented in FIG. 17, in the tissue-fastening tool 2, the distal end portion of the stylet 5 and the proximal end portion of the tissue-fastening tool 2 are engaged with each other inside the needle tube insertion passage 41 of the distal end portion of the needle tube 4 inserted into the sheath 3. The tissue-fastening tool 2 is provided to be projectable and retractable from the distal end of the needle tube 4. As represented in FIG. 17, a part of the tissue-fastening tool 2 located on a side closer to the distal end than the connection part with the stylet 5 protrudes from the distal end of the needle tube 4 and is disposed in a state in which a coil shape thereof is restored.

The main manipulation part 6 is packed as a product in a state in which the jig 9 is inserted from the proximal end side thereof.

If the state in which the entire tissue-fastening tool 2 is loaded in the needle tube 4 is set as a packing state, a state in which the tissue-fastening tool 2 is extended by the needle tube 4 continues for a long period of time. As a result, there is a possibility that a restoring force applied to the tissue-fastening tool 2 in advance to restore the coiled curved shape is weakened. When the tissue-fastening tool 2 is independently packed separately from the main manipulation part 6, it is necessary for a user to perform a task of coupling the proximal end portion of the tissue-fastening tool 2 and the distal end portion of the stylet 5. However, since the tissue-fastening tool 2 is a very small member, the coupling task requires skill and time.

In consideration of the reduction of the shape restoring force of the tissue-fastening tool 2 and difficulty of a loading task, in the present embodiment, as described above, the packing is performed in a state in which only the proximal end side region 26 of the tissue-fastening tool 2 engaged with the stylet 5 is inserted into the needle tube 4, and the distal end side region 25 is exposed from the needle tube 4. This state is referred to as an initial state in this description. An example of a procedure for setting the initial state will be described below.

When the stylet 5 is moved to the extreme distal side, the distal end engagement part 51 is exposed from the needle tube insertion passage 41. In this state, the initial state (packing state) is set by the protruding part 51*b* being engaged with the recessed part 24 of the tissue-fastening tool 2 and by the stylet 5 being moved to the proximal end side to store the distal end engagement part 51 in the needle tube 4. In the initial state, a connection state between the tissue-fastening tool 2 and the stylet 5 is maintained. At this time, a motion of pulling the stylet 5 using the jig 9 is performed.

Figure 18:
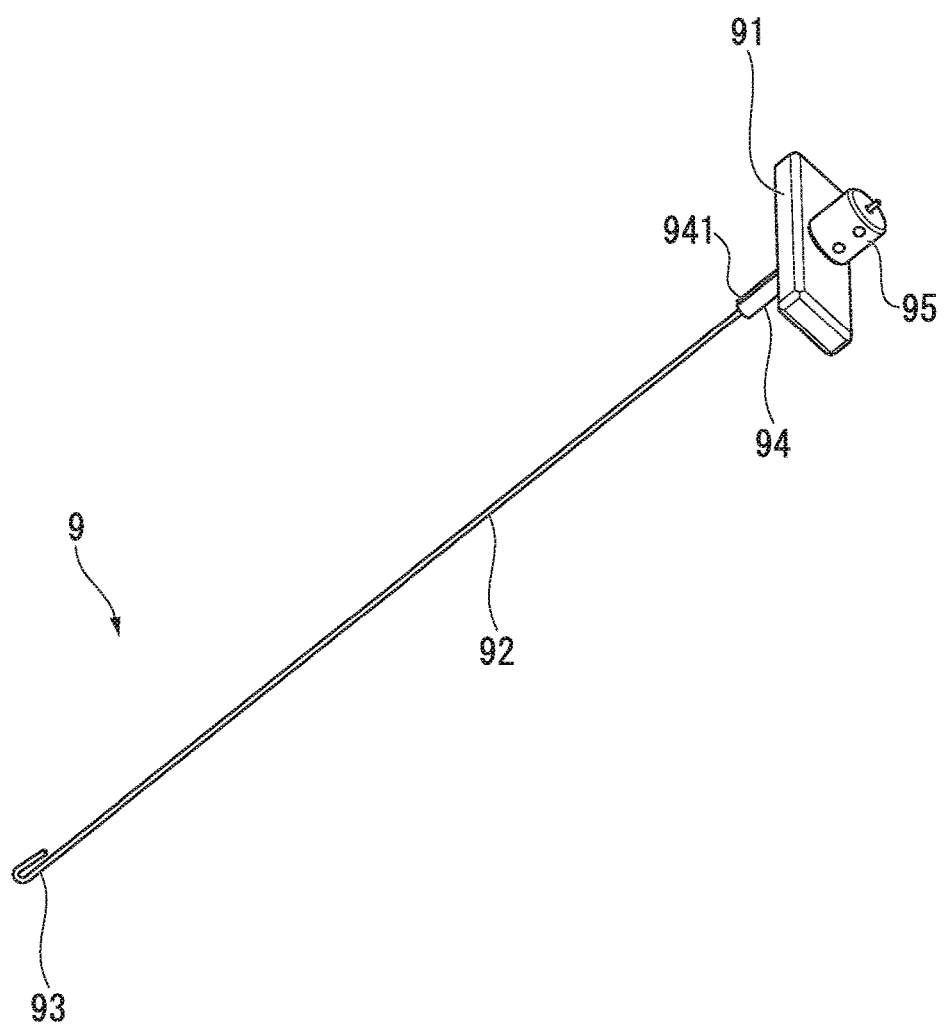
FIG. 18 is a perspective view of a jig according to the embodiment of the present invention.

The jig 9 is mounted on the main manipulation part 6 in the initial state (the packing state). FIG. 18 is a perspective view representing the jig 9. As represented in FIG. 18, the jig 9 includes a jig handle 91, a rod-like insertion shaft (a shaft) 92, a jig side coupling part 93, and a shaft head 95. The insertion shaft 92 is fixed to a distal end side of the shaft head 95. At the center of the jig handle 91, an open hole which is slightly larger than a diameter of the insertion shaft 92 and smaller than the shaft head 95 is formed, and the insertion shaft 92 is inserted through the hole. The jig side coupling part 93 has a hook shape which is curved from a distal end of the insertion shaft 92 and extends toward a proximal end side thereof. The jig handle 91 is provided to be relatively rotatable with respect to the insertion shaft 92. A tubular jig stopper 94 is externally mounted on an outer circumferential surface of a proximal end portion of the insertion shaft 92.

In the initial state, the jig side coupling part 93 is locked to the through-hole of the proximal end engagement part 56 in the first cam tube 61. That is, the tissue-fastening tool 2 and the jig 9 are connected to each other via the stylet 5.

The proximal end engagement part 56 is disposed on the distal end side of the first cam tube 61. The insertion shaft 92 passes through the inside of the first cam tube 61 and extends toward the proximal end side, and the jig handle 91 is exposed to the proximal side of the main manipulation part 6. At this time, the jig stopper 94 is not externally mounted on the insertion shaft 92. The insertion shaft 92 has a length that is greater than or equal to a length from the proximal end engagement part 56 to the proximal end of the Luer joint 57 when the stylet 5 is located at the extreme distal side with respect to the needle tube 4. At this time, since the distal end of the stylet 5 is exposed to the outside of the needle tube 4 as described above, the distal end of the stylet 5 is engaged with the tissue-fastening tool 2. The proximal end side region 26 of the tissue-fastening tool 2 is drawn into the needle tube 4 by pulling the jig 9 slightly toward the proximal end side to set the initial state. However, since there is a risk that the jig 9 moves toward the distal side and the tissue-fastening tool 2 is detached in this state, the jig stopper 94 is mounted to prevent the jig 9 from moving to the distal side in order to prevent the risk. Since a notch 941 is formed on the jig stopper 94 in the direction of the central axis L, the jig stopper 94 can be externally mounted on the insertion shaft 92 from a side thereof. Thus, the initial state (the packing state) is completed. After being sterilized by the manufacturer, a product is shipped.

First, a user performs a preparatory process (step S1) of pulling and entirely putting the tissue-fastening tool 2 into the needle tube 4. Here, the term "a user" refers to an operator and an assistant who assists a treatment of the operator. The preparatory process may be performed by the operator or by the assistant. In the following description, a rotational direction when the user performs a rotational manipulation of each part of the main manipulation part 6 and the auxiliary manipulation part 7 is represented as a rotational direction viewed from the proximal end to the distal end in the direction of the central axis L.

First, the user rotates the first rotation knob 66 of the main manipulation part 6 in a right direction. When the first rotation knob 66 rotates in the right direction, the Luer joint 57 and the first cam tube 61 fixed to the Luer joint 57 move to the proximal end side. Since the first engaging pin 55 of the stylet 5 is engaged with both the first guide passage 612 and the guide slit 673 of the needle guide 67, when the first cam tube 61 moves toward the proximal end side, the stylet 5 also moves toward the proximal end side. As a result, the tissue-fastening tool 2 is pulled toward the proximal end side within the needle tube 4. When the user continues to rotate the first rotation knob 66 right, the female screw 661 comes in contact with a distal end side terminal of the male screw 572 of the Luer joint 57 screwed into the female screw 661, the first rotation knob 66 cannot rotate any more, and the movement of the Luer joint 57 to the proximal end side cannot be performed. Thus, the user perceives that the substantially intermediate part of the tissue-fastening tool 2 in the longitudinal direction has been drawn into the needle tube 4.

Next, the tissue-fastening tool 2 is drawn into the needle tube 4 using the jig 9. When the user pulls the jig handle 91 of the jig 9 toward the proximal side in the direction of the central axis L, a pulling force in a proximal end direction acts on the stylet 5. At this time, since the first engaging pin 55 slides along the first guide passage 612, the stylet 5 moves toward the proximal end side while rotating, and the tissue-fastening tool 2 is further drawn into the needle tube 4. The jig handle 91 is provided to be relatively rotatable with respect to the insertion shaft 92. Therefore, at a time of a manipulation in which the user pulls the jig handle 91 in the direction of the central axis L, the insertion shaft 92 relatively rotates with respect to the jig handle 91 to follow rotation of the stylet 5. At this time, since the first engaging pin 55 is also engaged with the guide slit 673 of the needle guide 67, the needle guide 67 is simultaneously rotated. Since the tissue-fastening tool 2 generates a strong force to return to an original coil shape thereof by being drawn into the needle tube 4, the needle tube 4 receives the strong force from the tissue-fastening tool 2. Therefore, the movement of the needle tube 4 in the rotational direction may be made to follow the movement of the tissue-fastening tool 2 in order to easily draw the tissue-fastening tool 2 into the needle tube 4. Therefore, the needle tube 4 is attached to the needle guide 67 to be relatively rotatable and not to be advanceable and retractable. The tissue-fastening tool 2 can be loaded into the needle tube 4 while rotating due to the motion of pulling the jig handle 91 toward the proximal end side in a linear direction along the central axis L.

When the user continues to further draw the jig 9 toward the proximal side, the tissue-fastening tool 2 is gradually stored in the needle tube 4, and one of the first engaging pins 55 that is disposed closest to the proximal end side comes in contact with an end face on the distal end side of the Luer joint 57 immediately after the distal end of the tissue-fastening tool 2 is stored in the needle tube 4. Therefore, the stylet 5 can no longer move toward the proximal end side, and the jig 9 can no longer be drawn toward the proximal side. As a result, the user perceives that the loading of the tissue-fastening tool 2 has been completed. At the same time, since the proximal end engagement part 56 is exposed to the outside, the operator releases the engagement between the jig 9 and the proximal end engagement part 56 to detach the jig 9. Thus, the preparatory process is completed.

In this way, in the indwelling device 1 according to the present embodiment, since the tissue-fastening tool 2 is loaded using the jig 9, it is not required to provide a mechanism for drawing the tissue-fastening tool 2 into the needle tube 4 in the main manipulation part 6, and it is possible to reduce a size of the main manipulation part.

Figure 19:
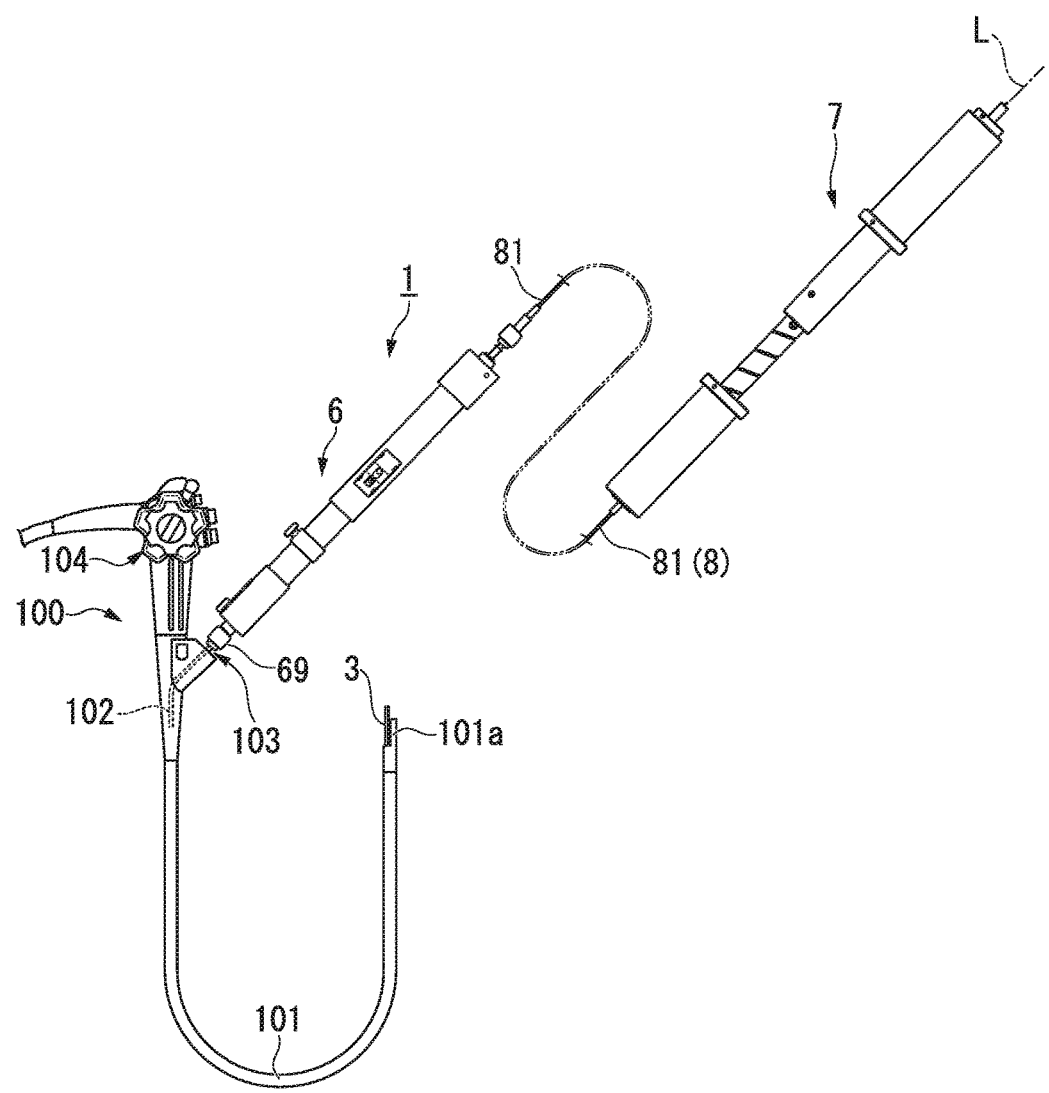
FIG. 19 is a diagram representing a state in which the tissue-fastening tool indwelling device according to the embodiment of the present invention is attached to an endoscope.

Next, the main manipulation part 6 is mounted on the endoscope 100 and fixed thereto (step S2). The sheath 3 and the needle tube 4 are inserted into the treatment tool channel 102 of the endoscope insertion part 101, and as represented in FIG. 19, the main manipulation part 6 is fixed to the manipulation part 104 of the endoscope 100 by the mounting part 69 provided at the distal end of the sheath slider 63 of the main manipulation part 6 being screw-engaged with the port 103 of the treatment tool channel 102 of the endoscope 100. In step S2, the operator and the assistant cooperate to perform the manipulation.

Figure 20:
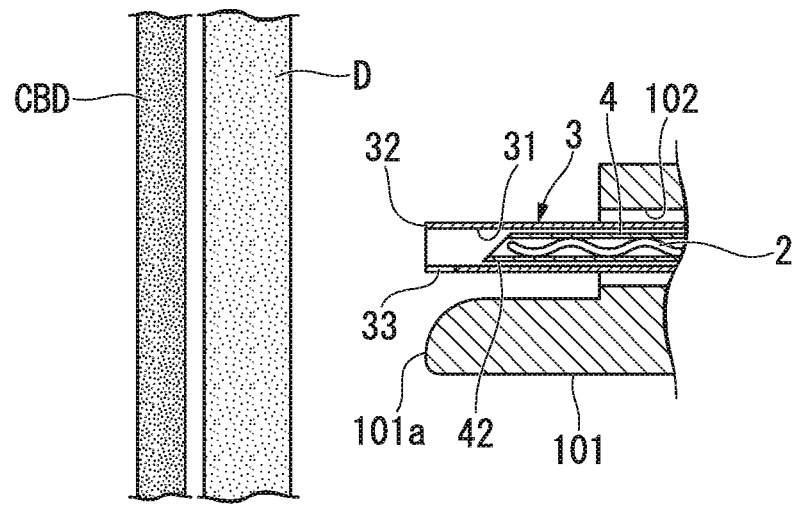
FIG. 20 is a side view representing a usage mode of the tissue-fastening tool indwelling device according to the embodiment of the present invention.

Manipulations from step S3 to step S9 are performed by the operator. FIGS. 20 to 26 are diagrams representing aspects on the distal end side of the endoscope insertion part 101 when using the indwelling device 1. As represented in FIG. 20, the operator inserts the endoscope insertion part 101 into a treatment target part in a body (step S3). A distal end of the endoscope insertion part 101 is inserted into the vicinity of the tissue D of the duodenum which is a target tissue. Steps S2 and S3 may be performed in reverse order.

Next, a position of the distal end of the sheath 3 with respect to the distal end of the endoscope insertion part 101 is adjusted (step S4). The operator loosens the fixing knob 634 and advances and retracts the main manipulation part main body 62 in the direction of the central axis L with respect to the sheath slider 63 to adjust the position of the distal end of the sheath 3 in the direction of the central axis L so that the position becomes a feasible position with respect to the distal end of the endoscope insertion part 101. FIG. 20 represents a state in which the distal end position of the sheath 3 in the direction of the central axis L coincides with the distal end of the endoscope insertion part 101. When the distal end position of the sheath 3 is determined, the operator tightens the fixing knob 634 to fix the position of the sheath 3.

Figure 21:
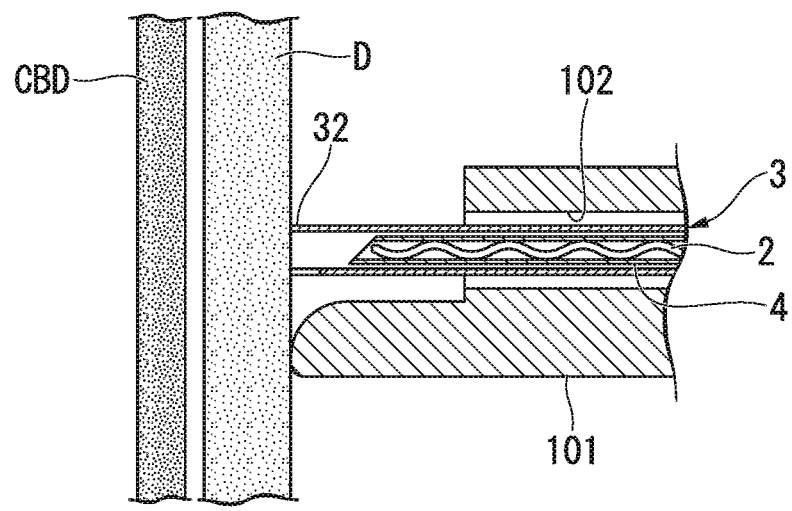
FIG. 21 is a side view representing the usage mode of the tissue-fastening tool indwelling device according to the embodiment of the present invention.

As represented in FIG. 21, the operator brings the endoscope insertion part 101 and the distal end opening portion 32 of the sheath 3 into contact with the tissue D of the duodenum. An ultrasonic transducer 101a is provided at the distal end of the endoscope insertion part 101. Therefore, in a subsequent treatment, a state in which the distal end of the endoscope insertion part 101 is in contact with the tissue D of the duodenum is maintained, and the operator performs the treatment while checking an ultrasonic image.

Subsequently, an amount of protrusion of the needle tube 4 from the distal end opening portion 32 of the sheath 3 in the direction of the central axis L is set (step S5). When the operator loosens the needle stopper screw 652, the needle slider stopper 65 can slide. After the operator slides the needle slider stopper 65 toward the distal side depending on a length (amount of protrusion of the needle tube 4 from the sheath 3) by which the puncturing part 42 of the needle tube 4 is desired to puncture into the tissue, the operator tightens the needle stopper screw 652 to fix the needle slider stopper 65. By the manipulation, a puncture length of the puncturing part 42 of the needle tube 4 is set. At this time, the movement of the needle slider 64 is restricted by the slide button unit 68, and the needle slider 64 does not move linearly.

Figure 22:
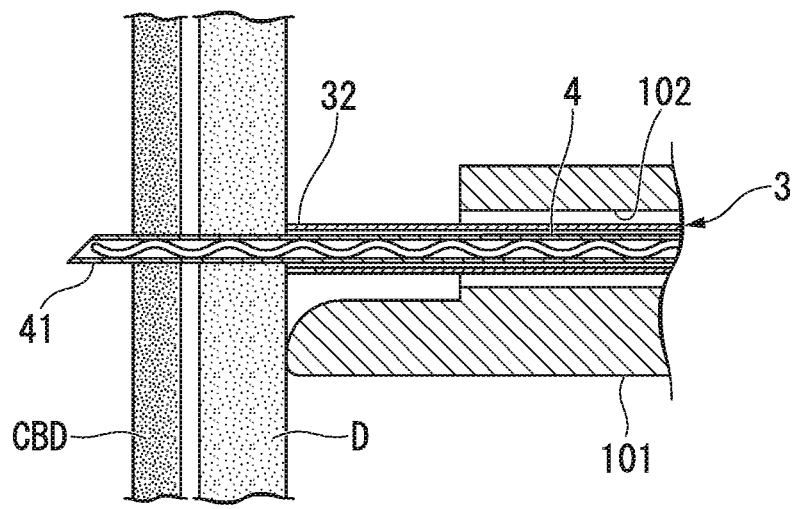
FIG. 22 is a side view representing the usage mode of the tissue-fastening tool indwelling device according to the embodiment of the present invention.

Next, as represented in FIG. 22, the puncturing part 42 of the needle tube 4 punctures the target tissue (step S6). When the operator pushes the button main body 682 of the slide button unit 68 toward the side of the central axis L, a restriction of an advancement and retraction movement of the needle slider 64 is released, and the needle slider 64 enters a state of being advanceable and retractable in the direction of the central axis L with respect to the main manipulation part main body 62. Thereafter, the operator advances the needle slider 64 in a linear direction until it comes into contact with the needle slider stopper 65. Since the needle slider 64 and the needle tube 4 are connected to each other via the needle guide 67 such that relative positions thereof in the direction of the central axis L are invariable, the needle tube 4 advances straight with the advancement of the needle slider 64. As a result, the puncturing part 42 of the needle tube 4 protrudes from the distal end of the sheath 3 and punctures the tissue D of the duodenum and the tissue CBD of the common bile duct, which are target tissues. When the operator releases (release the pressure to the button main body 682) his or her finger from the slide button unit 68, the slide button unit 68 moves in a direction which separates the button main body 682 from the outer side of the needle slider 64 in the radial direction by an urging force of the spring member 683, and the locking pin 684c is pressed against the outer surface of the main manipulation part main body 62.

Figure 23:
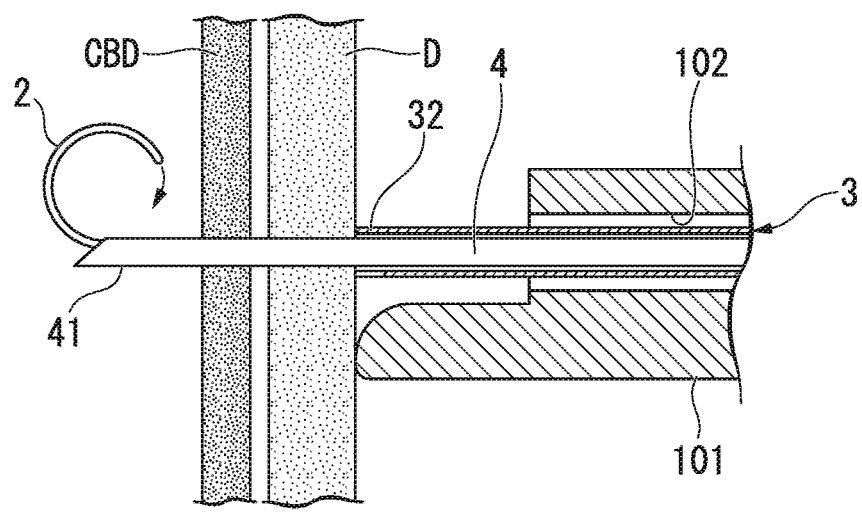
FIG. 23 is a side view representing the usage mode of the tissue-fastening tool indwelling device according to the embodiment of the present invention.

Next, the tissue-fastening tool 2 is indwelled into a common bile duct side (step S7). As represented in FIG. 23, the tissue-fastening tool 2 is caused to protrude from the needle tube 4. An operator rotates the first rotation knob 66 left. In a step in which a left rotational manipulation of the first rotation knob 66 is started, the needle slider 64 is also rotated left with the first rotation knob 66 until the locking pin 684c of the plate 684 is engaged with the helical groove 622 of the main manipulation part main body 62. Shortly, when the locking pin 684c is engaged with the helical groove 622, although the needle slider 64 about to advance toward the distal end side while rotating along the helical groove 622, the needle slider 64 neither rotates nor advances because the needle slider 64 is in contact with the needle slider stopper 65. For this reason, after the locking pin 684c is engaged with the helical groove 622, only the first rotation knob 66 is rotated. When the first rotation knob 66 is rotated with respect to the needle slider 64, the Luer joint 57 and the first cam tube 61 are linearly sent to the distal side. At this point, the end face of the distal end side of the Luer joint 57 and one of the first engaging pins 55 at the extreme proximal end side come into contact with each other. Thereby, the stylet 5 is linearly sent to the distal side while causing the first engaging pins 55 to slide along a slit surface of the guide slit 673 by pushing out the first engaging pins 55 by a distal end face of the Luer joint 57. As a result, a distal end side region 25 of a coil of the tissue-fastening tool 2 is linearly sent from the distal end of the needle tube 4 into the common bile duct. That is, in the first state, the stylet 5 in the needle tube 4 linearly advances the distal end side region 25 of the tissue-fastening tool 2 without rotating the distal end side region 25, so that the distal end side region 25 is capable of being sent from the distal end 42 of the needle tube 4 into the common bile duct.

When a proximal end side end face 573*a* of the linear groove 573 of the Luer joint 57 comes into contact with a proximal end side end face of the engaging projection 643*b* of the needle slider end member 643 in time, the Luer joint 57 does no longer move toward the distal end side, and the first rotation knob 66 does not rotate. The proximal end side end face 573*a* of the linear groove 573 of the Luer joint 57 functions as a restriction portion for restricting rotation of the first rotation knob 66. A length in the direction of the central axis L between the proximal end side end face 573*a* of the linear groove 573 of the Luer joint 57 and the proximal end side end face of the engaging projection 643*b* of the needle slider end member 643 is set depending on a predetermined length at which the distal end side region 25 of the tissue-fastening tool 2 is sent on the common bile duct side. For this reason, when the distal end 27 of the tissue-fastening tool 2 protrudes from a needle tip of the needle tube 4 and there is a positional relationship in which the proximal end 21 of the tissue-fastening tool 2 is located inside the needle tube 4, the proximal end side end face 573*a* of the linear groove 573 of the Luer joint 57 pushes onto the proximal end side end face of the engaging projection 643*b* of the needle slider end member 643, and the rotation of the first rotation knob 66 is restricted. As the first rotation knob 66 does not rotate, the operator can perceive that the process of indwelling the predetermined length of the coil of the tissue-fastening tool 2 on the common bile duct side is completed.

Figure 24:
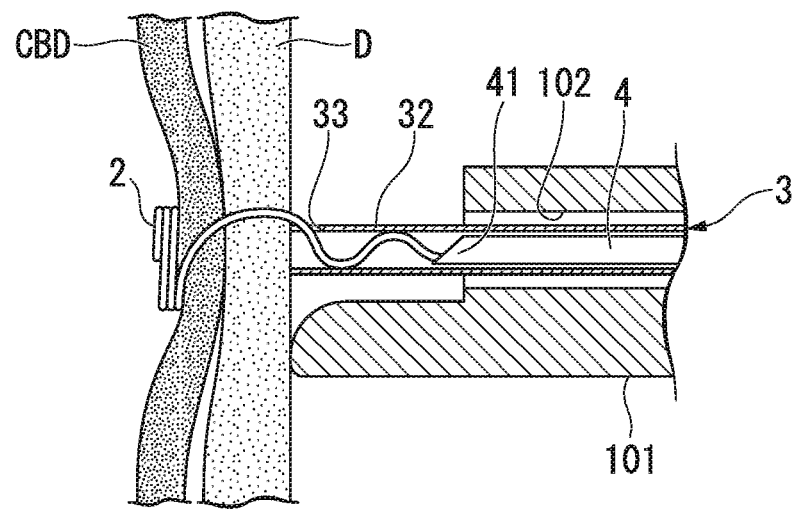
FIG. 24 is a side view representing the usage mode of the tissue-fastening tool indwelling device according to the embodiment of the present invention.

Next, as represented in FIG. 24, the needle tube 4 is removed from the tissue CBD of the common bile duct and the tissue D of the duodenum (step S8). When the needle tube 4 is removed, as the distal end of the needle tube 4 is pulled out of the tissue CBD of the common bile duct, a coil part 2*a* of the tissue-fastening tool 2 is inclined and a circumferential direction of the coil comes into close contact with the tissue CBD of the common bile duct. At this time, since there is a case in which the coil part 2*a* is inclined in a direction different from a predetermined direction of the coil, a manipulation of correcting a direction of the coil part 2*a* to the predetermined direction is necessarily performed.

The operator rotates the needle slider 64 right. Since the locking pin 684*c* of the plate 684 is engaged with the helical groove 622 of the main manipulation part main body 62, when the needle slider 64 is rotated right, the needle slider 64 moves toward the proximal side while rotating along the helical groove 622. The Luer joint 57 and the first cam tube 61 also move toward the proximal side integrally with the needle slider 64 while rotating right. Since the first guide passage 612 of the first cam tube 61 is formed in a right screw direction, an inner surface of the first guide passage 612 imparts a vector force in a direction of the proximal side to the first engaging pin 55 of the stylet 5 due to a right rotation of the first cam tube 61. When the operator moves the needle slider 64 to the extreme proximal side while rotating the needle slider 64, the locking pin 684*c* passes over the aforementioned oblique portion 622*a* and is fitted into the dent portion 622*b*. For this reason, as long as the operator does not press the button main body 682 inward in a radial direction to be pushed in until the button main body 682 comes into contact with the base body 681, the fitting of the locking pin 684*c* into the dent portion 622*b* is not capable of being intentionally released, and the needle slider 64 is not capable of being advanced.

Since one of the first engaging pins 55 on the extreme proximal end side is in contact with the end face on the distal end side of the Luer joint 57, the stylet 5 basically moves toward the proximal end side while rotating right together with the needle slider 64. At this time, the needle guide 67 also moves toward the proximal end side while rotating right together with the needle slider 64. Since the needle tube 4 is rotatably supported by the needle guide 67, the needle tube 4 moves toward the proximal end side together with the needle slider 64, but the movement of the needle tube 4 in the rotational direction is not related to the needle slider 64. In an actual procedure, since the endoscope insertion part 101 has a complex curved shape, the needle tube 4 inserted into the treatment tool channel 102 is also curved into a complicated shape. As described above, a material of the needle tube 4 is a metal tube, and it is difficult to perform a manipulation which rotates the needle tube 4 in a state of being curved into the complicated shape because a very strong force is necessary. Therefore, even if the needle slider 64 moves toward the proximal end side while rotating, the needle tube 4 is configured to only follow movement toward the proximal end side without rotating.

As represented in FIG. 6A, the sheath 3 is fixed to the sheath guide 623 via the sheath fixing part 625. The sheath guide 623 is rotatably supported by the main manipulation part main body 62. As represented in FIG. 6D, the first slit 623*b* of the sheath guide 623 is fitted onto the rib 673*a* formed on the radial outside of the circumference of the guide slit 673 of the needle guide 67 to follow only the rotational direction. With such a configuration, when the needle slider 64 is moved toward the proximal end side while being rotated right, the sheath 3 only follows the rotation.

With the aforementioned motion, the sheath 3 and the stylet 5 rotate while the needle tube 4 is pulled back. When the puncturing part 42 of the needle tube 4 is stored in the lumen 31 of the sheath 3, the wire of the tissue-fastening tool 2 enters the notched part 33 of the sheath 3. When the sheath 3 rotates in a predetermined direction in a state in which the wire of the tissue-fastening tool 2 is locked to the notched part 33, the coil part 2*a* indwelled in the common bile duct side rotates, and the direction of the coil part 2*a* is corrected to a desired state.

As described above, in step S8, the stylet 5 moves toward the proximal end side while rotating, and at the same time, the needle tube 4 moves toward the proximal end side without rotating. By this manipulation, since the stylet proximal end member 54 to which the stylet 5 is connected receives from the first cam tube 61 a vector in the direction toward the proximal end side, the stylet 5 and the needle tube 4 are pulled back toward the proximal end side. At this time, in a state in which the distal end opening portion 32 of the sheath 3 comes into contact with the target tissue, the coil part 2*a* of the tissue-fastening tool 2 indwelled in the common bile duct side acts as an anchor, and the tissue-fastening tool 2 simultaneously receives a force pulling in a direction of the distal end. When a force which pulls the stylet 5 toward the proximal end side increases, there is a risk that a force applied to the target tissue by the target tissue being sandwiched between the tissue-fastening tool 2 and the sheath 3 becomes stronger and the tissue is compressed due to an excessive load.

In the indwelling device 1 according to the present embodiment, in order to prevent an excessive load to the target tissue, when a force sandwiching the target tissue between the tissue-fastening tool 2 and the sheath 3 becomes stronger, synchronization of the stylet 5 with the movement of the needle slider 64 moving in the proximal direction while rotating right is released, and the force sandwiching the target tissue between the tissue-fastening tool 2 and the sheath 3 is relieved. As described above, the first guide passage 612 imparts a vector force in a direction of the proximal side to the first engaging pin 55 of the stylet 5. However, when a force in the distal direction from the tissue-fastening tool 2 becomes stronger than the vector force, the synchronization between the stylet 5 and the needle slider 64 is released, only the needle tube 4 moves toward the proximal side, and the first engaging pin 55 moves in the distal direction along the first guide passage 612. At this time, since the stylet 5 relatively moves to the distal end side with respect to the needle slider 64, the load can be weakened. As a result, if the force toward the distal direction from the tissue-fastening tool 2 is lower than the vector force in the proximal direction, the stylet 5 enters a state of following the movement of the needle slider 64 again. In this way, it is possible to prevent damage to the tissue of the treatment target site. A motion of automatically adjusting the load can be achieved by suitably setting the lead angle of the first guide passage 612. Specifically, the motion can be achieved by setting the lead angle within the range of 20 degrees to 75 degrees.

When the lead angle of the first guide passage 612 is smaller than 20 degrees, since the vector force in the proximal side direction imparted to the first engaging pin 55 becomes stronger, forces are first balanced when the force in the distal direction from the tissue-fastening tool 2 becomes very strong. Thus, there is a possibility that the sandwiched tissue is damaged. When the lead angle of the first guide passage 612 is larger than 75 degrees, since the vector force in the proximal side direction imparted to the first engaging pin 55 becomes weaker, the forces are balanced in a state in which the force in the distal direction from the tissue-fastening tool 2 is very weak. Thus, there is a possibility that the stylet 5 cannot be sufficiently pulled toward the proximal side. Further, it is more preferable that the lead angle be in the range of 40 degrees or more. This is because the larger the lead angle is, the smaller the diameter of the first cam tube 61 can be set. By reducing the diameter of the first cam tube 61, it is possible to reduce the diameter and weight of the main manipulation part 6.

In step S8, when the locking pin 684c moves toward the proximal end of the helical groove 622, the needle slider 64 is not rotated, and thus the operator can perceive that the needle tube 4 is removed from the tissue. As described above, due to the needle anti-movement mechanism that prevents the needle slider 64 from being advanced while being rotated again, the needle slider 64 can be neither advanced nor retracted while being rotated.

Figure 25:
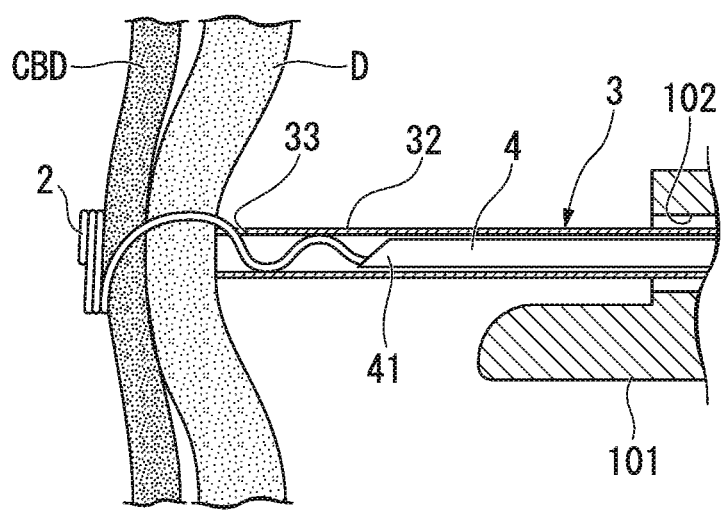
FIG. 25 is a side view representing the usage mode of the tissue-fastening tool indwelling device according to the embodiment of the present invention.

Next, as represented in FIG. 25, the sheath 3, the needle tube 4, and the stylet 5 are advanced by a predetermined distance (step S9). In a state in which the distal end portion of the sheath 3 comes into contact with the tissue D of the duodenum, the operator loosens the fixing knob 634 and advances the fixing knob 634 until the fixing knob 634 comes into contact with the distal end of the second slit 633. Thus, the main manipulation part main body 62 comes into contact with the distal end of the sheath slider 63. By this manipulation, the distal end part of the sheath 3 protrudes from the distal end of the treatment tool channel 102.

Since the mounting part 69 is fixed to the endoscope 100, the sheath 3 is extruded from the distal end of the endoscope insertion part 101, and the endoscope insertion part 101 relatively retracts and the distal end thereof is separated from the tissue D of the duodenum. In the subsequent treatment, a surgical field is imaged by an optical imaging device (not represented) provided at the distal end of the endoscope insertion part 101. The operator performs the treatment while checking the endoscopic image.

In step S9, a force in a direction of retracting toward the proximal side is generated in the main manipulation part main body 62. However, since the screw part 634a of the fixing knob 634 is pressed by the resin spring 635 of the sheath slider 63, it is possible to prevent the main manipulation part main body 62 from retracting.

Since the main manipulation part main body 62 can no longer advance when the main manipulation part main body 62 comes into contact with the sheath slider 63, the operator can perceive that the main manipulation part main body 62 has been pushed into a predetermined position. Further, since the main manipulation part main body 62 does not unintentionally move toward the proximal side due to the function of the resin spring 635 even if the fixing knob 634 is not tightened, the position of the main manipulation part main body 62 does not deviate from the predetermined position.

The next step S10 is performed by the assistant and the operator cooperating. Manipulations subsequent to step S11 are performed by the assistant manipulating the auxiliary manipulation part 7. That is, the manipulation of sending the coil of the tissue-fastening tool 2 to the duodenum side is performed by the auxiliary manipulation part 7.

The auxiliary manipulation part 7 is connected to the main manipulation part 6 (step S10). The assistant holds the auxiliary manipulation part 7 and inserts the proximal end of the Luer joint 57 of the main manipulation part 6 into a distal end opening of the sixth insertion passage 711 of the manipulation coupling part 71. When the operator or the assistant rotates the manipulation coupling part 71, the screw groove 712 of the sixth insertion passage 711 and the flange 574 formed at the proximal end portion of the Luer joint 57 are screwed together, and the main manipulation part 6 and the auxiliary manipulation part 7 are connected to each other. When the rotation handle 74 is rotated right, the rotation handle 74 advances while rotating to follow the second guide passage 731 formed in the second cam tube 73. Since the transmission member 8 is fixed to the rotation handle 74 via the fixing member 744, the transmission member 8 advances while rotating right. Since the stylet engagement part 82 of the transmission member 8 advances while rotating, the stylet engagement part 82 comes into contact with the proximal end engagement part 56 of the stylet 5 in a short time. As represented in FIG. 8, the proximal end portion 56a has a shape that protrudes toward the proximal side on the central axis L. Therefore, in a state in which the stylet engagement part 82 of the transmission member 8 and the proximal end of the proximal end engagement part 56 of the stylet 5 come into contact with each other, the transmission member 8 advances while rotating. Thus, the proximal end engagement part 56 of the main manipulation part 6 is fitted and engaged between the two arms 82b of the stylet engagement part 82. Thereafter, the rotation and the advance driving of the transmission member 8 can be transmitted to the stylet 5.

As represented in FIG. 19, since the main manipulation part 6 and the auxiliary manipulation part 7 are coupled to each other by a flexible part including the cable tube 81 and the transmission member 8, adaptability can be given to a positional relationship between the main manipulation part 6 and the auxiliary manipulation part 7. Thus, the assistant can perform the manipulation without disturbing the operator by standing at a location where it is easy to operate the auxiliary manipulation part 7. Since there is the flexible part between the main manipulation part 6 and the auxiliary manipulation part 7, the main manipulation part 6 is not strongly pushed even if the assistant strongly pushes the auxiliary manipulation part 7 in the distal direction of the central axis L.

As described above, as represented in FIGS. 13 and 15, the fitting hole 733, into which the rod-like member 734 is insertable, is exposed when the rotation handle 74 is moved to the extreme proximal side. For this reason, the rod-like member 734 is fitted into the fitting hole 733 formed in the second cam tube 73, and thereby the rod-like member 734 is allowed to protrude outward in the radial direction of the second cam tube 73. Therefore, the rod-like member 734 is merely fitted into the fitting hole 733, and thereby the rotation handle 74 of the auxiliary manipulation part 7 can be prevented from being rotated unintentionally.

Further, in a state in which the needle tube 4 is removed from the two types of luminal tissue including the tissue D of the duodenum and the tissue CBD of the common bile duct, the needle slider 64 is prevented from being advanced again by the aforementioned needle anti-movement mechanism. Therefore, for example, when an assistant manipulates the auxiliary manipulation part 7, the needle tube 4 is prevented from being pushed out to the distal end side unintentionally.

Next, the tissue-fastening tool 2 is indwelled in a lumen constituted of the tissue D of the duodenum (step S11). When the assistant rotates the rotation handle 74 to right, the transmission member 8 advances while rotating right.

Specifically, as represented in FIG. 14A, when the rotation handle 74 is rotationally manipulated, the second engaging pin 743 moves along the inside of the second guide passage 731, and the rotation handle 74 relatively moves to the distal side with respect to the second cam tube 73 and approaches the auxiliary manipulation part main body 72. Further, when the rotation handle 74 is rotationally manipulated, the distal end portion of the rotation handle 74 enters the gap S between the second cam tube 73 and the auxiliary manipulation part main body 72 inside the first region 721a of the seventh insertion passage 721.

As described above, when the rotation handle 74 is rotationally manipulated, the transmission member 8 is configured to advance while rotating with respect to the auxiliary manipulation part 7 and to protrude from the manipulation coupling part 71. As a result, helical movement (helical input) of the transmission member 8 is transmitted to the stylet 5. Then, the first engaging pins 55 begin to be separated from the distal end face of the Luer joint 57. Since the rotation handle 74 rotates the stylet 5 while advancing the stylet 5 with respect to the Luer joint 57, the first engaging pins 55 are rotated while engaged with the slit surface of the guide slit 673 in the rotational direction of the stylet 5. At the same time, the first engaging pins 55 slide along the first guide passage 612 of the first cam tube 61. Thereby, the proximal end side region 26 of the tissue-fastening tool 2 is advanced while being rotated, and can be sent from the distal end of the needle tube 4 into the duodenum.

The helical pitch P1 of the first guide passage 612 of the first cam tube 61 is equal to the helical pitch P2 of the second guide passage 731 of the second cam tube 73. Rotational directions of the first guide passage 612 and the second guide passage 731 are also equal to each other in the right direction. The indwelling device 1 is provided with the main manipulation part 6 and the auxiliary manipulation part 7 as separate bodies, and the manipulation of the auxiliary manipulation part 7 is transmitted to the main manipulation part 6 via the transmission member 8. Further, in consideration of manipulation properties when the main manipulation part 6 and the auxiliary manipulation part 7 are manipulated by different persons, the transmission member 8 may have flexibility and may have a long length in some cases. In such cases, there is a deviation between the movement of the rotation handle 74 and the movement of the stylet engagement part 82 due to an influence of bending and length of the transmission member 8 in the transmission path of the driving force, so that there is a possibility that movement may not be accurately transmitted to the stylet 5.

However, in the indwelling device 1 according to the present embodiment, since the first guide passage 612 and the second guide passage 731 are formed at the same helical pitch and in the same rotational direction, a rotating motion transmitted from the transmission member 8 can be adjusted to be the same rotational movement amount as the movement of the rotation handle 74 in the first guide passage 612. Therefore, an input in a helical direction generated by the rotational manipulation of the auxiliary manipulation part 7 is accurately output from the stylet 5 as a helical motion.

Figure 26:
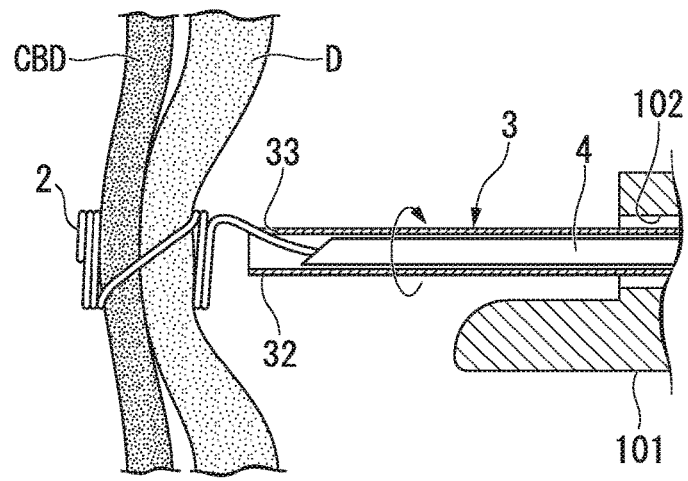
FIG. 26 is a side view representing the usage mode of the tissue-fastening tool indwelling device according to the embodiment of the present invention.

As described above, when the rotation handle 74 is rotationally manipulated, the first engaging pin 55 of the stylet 5 rotates the needle guide 67 and the needle guide 67 rotates the sheath guide 623. Thus, the sheath 3 rotates in synchronization with the rotation of the stylet 5. As illustrated in FIG. 26, in step S11, since the tissue-fastening tool 2 enters the notched part 33 of the sheath 3, the tissue-fastening tool 2 is pushed out from the needle tube 4 while being rotated by the sheath 3 and the stylet 5. At this time, the needle tube 4 does not rotate as described above. When the one of the first engaging pins 55 of the stylet 5 at the extreme distal end side comes into contact with the distal end of the first guide passage 612 of the first cam tube 61, the advancement of the stylet 5 is completed. At this time, the distal end of the stylet 5 is exposed to the outside of the needle tube 4. Thus, the engagement between the implant-coupling part 22 of the tissue-fastening tool 2 and the distal end engagement part 51 of the stylet 5 is released, and the indwelling of the tissue-fastening tool 2 is completed. As described above, the indwelling device 1 is configured such that the distal end of the stylet 5 is exposed from the distal end of the needle tube 4 when both of the main manipulation part 6 and the auxiliary manipulation part 7 perform the motion (the first motion) in which the tissue-fastening tool 2 is discharged from the distal end of the needle tube 4 by the stylet 5 being advanced with respect to the needle tube 4.

According to the present embodiment, after the needle tube 4 is removed from the tissue and stored in the sheath 3, coil indwelling on the duodenum side is performed by the auxiliary manipulation part 7. That is, it is possible to separately perform a plurality of manipulations of the main manipulation part 6 and the auxiliary manipulation part 7 to indwell the tissue-fastening tool 2 in the treatment target tissue. Thus, the main manipulation part 6 can be reduced in size in comparison to a conventional implant-indwelling device. Therefore, it is possible to improve manipulation properties of the operator.

Further, the manipulation related to the advancement and retraction of the needle tube 4 can be performed only by the main manipulation part 6, and the manipulation caused by the auxiliary manipulation part 7 is performed in a state in which the puncturing part 42 of the needle tube 4 is stored in the sheath 3. When the coil of the tissue-fastening tool 2 is indwelled at the duodenum side, the locking pin 684c passes over the oblique portion 622a and is fitted into the dent portion 622b. In this state, as long as the operator does not press the button main body 682 inward in the radial direction to be pushed in until the button main body 682 comes into contact with the base body 681, the state in which the locking pin 684c is fitted into the dent portion 622b is maintained. For this reason, as long as the operator does not intentionally press the button main body 682 inward in the radial direction, the needle slider 64 can be neither advanced nor retracted. Thus, the operator easily controls the movement of the needle tube 4. In addition, the needle tube 4 is affected by the manipulation of the assistant, the needle tube 4 (the puncturing part 42) does not move unintentionally caused by a manipulation of the assistant. For this reason, the puncturing part 42 does not damage the tissue.

According to the present embodiment, the main manipulation part is provided with the first helical mechanism, and the auxiliary manipulation part is provided with the second helical mechanism. Therefore, it is possible to output a manipulation that is input to the auxiliary manipulation part to the manipulation transmission member as a motion of the second helical mechanism in a predetermined helical direction. In addition, a motion which is input from the manipulation transmission member to the main manipulation part is once adjusted due to passing through the first helical mechanism, and is output as a motion in the predetermined helical direction from the stylet. Therefore, even if there is an error in an input motion input to the auxiliary manipulation part and an output motion output from the auxiliary manipulation part caused by a long drive transmission path between the main manipulation part and the auxiliary manipulation part, it is possible to adjust the error by the first helical mechanism again. Therefore, a helical motion which is input to the auxiliary manipulation part is transmitted to the tissue-fastening tool via the main manipulation part with high accuracy.

According to the present embodiment, since the lead angle of the first guide passage is set in the range of 20 degrees or more and 75 degrees or less, when a force sandwiching a target tissue between the tissue-fastening tool and the sheath becomes stronger, synchronization between the retraction of the needle tube and the retraction of the stylet is released. Therefore, it is possible to prevent an excessive load from being applied to the target tissue when removing the needle tube. More preferably, the lead angle is set in the range of 40 degrees or more. Since this enables a decrease in the diameter of the first cam tube, it is possible to reduce the diameter and weight of the main manipulation part.

According to the present embodiment, since the state in which the tissue-fastening tool is protruded from the distal end of the needle tube and packed is the initial state, the state in which the tissue-fastening tool is stretched within the needle tube for a long period of time is not maintained, and the fastening force of the tissue-fastening tool can be maintained in a suitable state.

Further, the tissue-fastening tool in the packing state can be easily loaded using the jig. In the indwelling device according to the present embodiment, since the tissue-fastening tool is loaded using the jig, there is no need to provide the main manipulation part with a mechanism which draws the tissue-fastening tool into the needle tube, and the size of the main manipulation part can be reduced.

Although the present embodiment describes the configuration in which the main manipulation part 6 and the auxiliary manipulation part 7 can be separated as an example, the main manipulation part and the auxiliary manipulation part may be configured to be inseparable, for example, by integrally configuring the stylet 5 and the transmission member 8.

The present embodiment describes an example in which the protruding part 51b is provided on the distal end engagement part 51, the recessed part 24 is provided in the implant-coupling part 22, and the stylet 5 and the tissue-fastening tool 2 are connected to each other by the protruding part 51b being engaged with the recessed part 24. However, a configuration in which the recessed part is provided in the distal end engagement part and the protruding part is provided in the implant engagement part may be adopted.

Although the present embodiment describes an example in which the three first engaging pins 55 are provided on the stylet proximal end member 54, the number of the first engaging pins is not limited to three, and at least one first engaging pin may be provided.

Although the present embodiment describes an example in which the first guide passage 612 is a hole communicating the inside and outside of the first cam tube 61 and the second guide passage 731 is a groove having a bottom formed on the outer circumferential surface of the second cam tube 73, for example, the second guide passage may be a hole.

<First Modified Example>

In the above embodiment, the example in which the Luer joint 57 and the first rotation knob 66 are threadedly engaged by the male screw 572 and the female screw 661 is given, but the threadedly engaging structure of the Luer joint 57 and the first rotation knob 66 is not limited thereto. In the above embodiment, the example in which the movement of the Luer joint 57 to the distal side is restricted by bringing the proximal end side end face of the linear groove 573 of the Luer joint 57 into contact with the proximal end side end face of the engaging projection 643b of the needle slider end member 643 is given, but the structure for restricting the movement of the Luer joint 57 to the distal side is not limited thereto.

Figure 27:
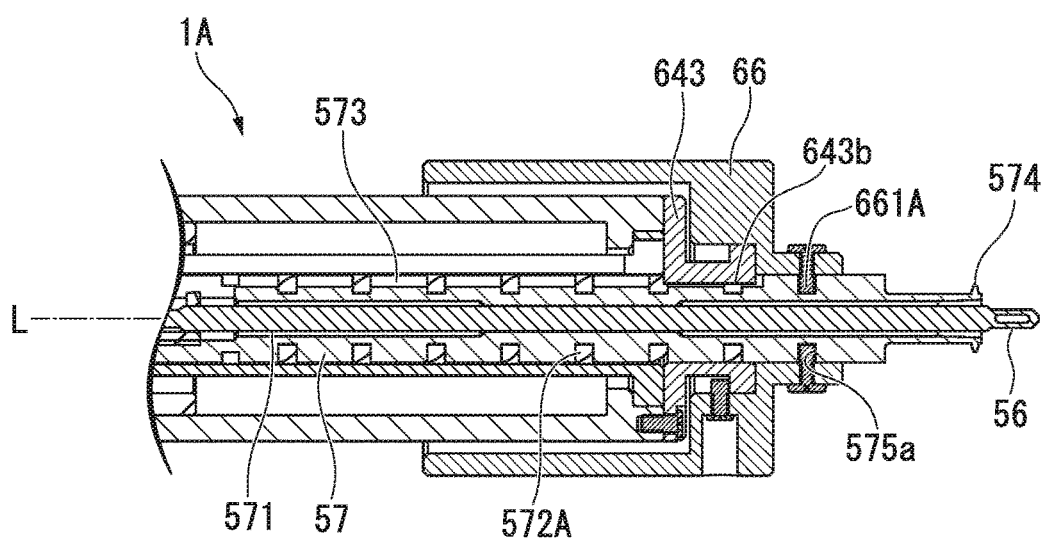
FIG. 27 is a view representing a modified example of a screwing structure of a Luer joint and a first rotation knob of the embodiment of the present invention.

A modified example of the threadedly engaging structure of the Luer joint 57 and the first rotation knob 66 is represented in FIG. 27. As represented in FIG. 27, an indwelling device 1A may be configured to be threadedly engaged by a third helical groove 572A and a projection 661A instead of the male screw 572 and the female screw 661 of the above embodiment. In this case, the third helical groove 572A is formed in an outer circumference of the Luer joint 57. That is, in the present modified example, a step that extends in a helical shape is formed on the outer circumference of the Luer joint by the third helical groove 572A. The projection 661A is a sliding portion that protrudes inward from an inner circumference of the first rotation knob 66 in a radial direction and is slidable while being engaged with the step. The third helical groove 572A is configured such that the projection (the sliding portion) 661A slides along the third helical groove 572A while engaged.

In the case of the present modified example, a proximal end face 575a of the third helical groove 572A is formed at the proximal end side of the Luer joint 57. That is, the proximal end face 575a is an end face provided at a terminal of the step formed by the third helical groove 572A, and the projection (the sliding portion) 661A of the first rotation knob 66 abuts this end face, and thereby functions as a restriction portion for restricting the rotation of the first rotation knob 66. In this case, the projection (the sliding portion) 661A of the first rotation knob 66 abuts the proximal end face 575a, and thereby the stylet 5 is restricted not to advance straight. Further, in the state in which the projection (the sliding portion) 661A of the first rotation knob 66 abuts the proximal end face 575a, the distal end 27 of the tissue-fastening tool 2 protrudes from the needle tip of the needle tube 4, and the proximal end 21 of the tissue-fastening tool 2 is located inside the needle tube 4. In this case, the proximal end side end face of the linear groove 573 of the Luer joint 57 does not come into contact with the proximal end side end face of the engaging projection 643b of the needle slider end member 643.

When an operator rotates the first rotation knob 66 in the right direction, the Luer joint 57 and the first cam tube 61 fixed to the Luer joint 57 move to the distal side. This movement is the same as in the above embodiment in which the male screw 572 and the female screw 661 are threadedly engaged.

The third helical groove 572A may be formed with two helical grooves at positions that are opposite to each other in a radial direction, and two projections (sliding portions) 661A that slide while being engaged with the two helical grooves may be formed.

<Second Modified Example>

Figure 28:
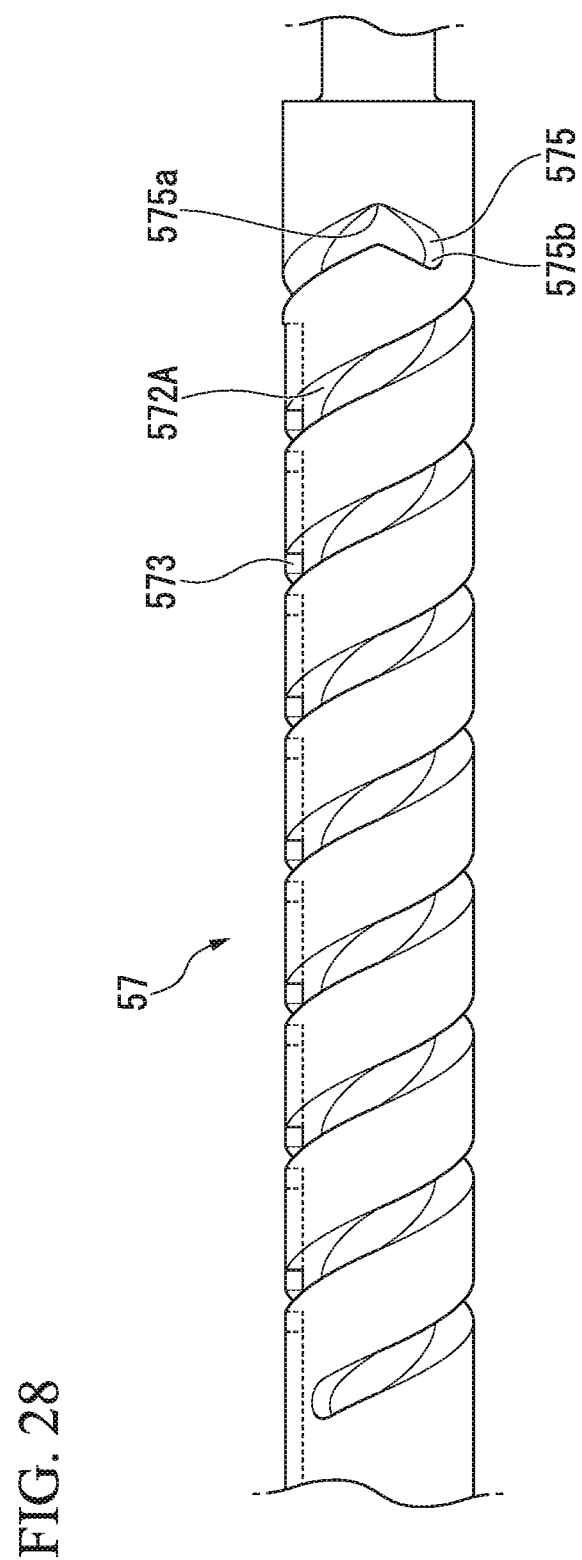
FIG. 28 is a view representing a proximal end portion of a third screwing groove of the Luer joint of FIG. 27.

Further, in addition to the structure described in the first modified example, a turnback groove may be formed in a proximal end of the third helical groove 572A of the Luer joint 57. For example, as represented in FIG. 28, the turnback groove is a first turnback groove 575 at which the proximal end portion of the third helical groove 572A is turned back from the proximal end side toward the distal end side of the Luer joint 57. The first turnback groove 575 is bent such that a groove extends from the proximal end toward a distal end side of the third helical groove 572A. The first turnback groove 575 has a proximal end face (a turnback proximal end) 575a of the third helical groove 572A, and a turnback distal end (a first locking surface) 575b located at more distal side than the proximal end face 575a. A length between the proximal end face (the turnback proximal end) 575a and the turnback distal end 575b is sufficiently short over the full length of the third helical groove 572A. Accordingly, a distance in the direction of the central axis L between the proximal end face (the turnback proximal end) 575a and the turnback distal end 575b is also sufficiently short. When the first rotation knob 66 is rotated left, the Luer joint 57 moves to the distal side, and the projection 661A reaches the first turnback groove 575 in time. Then, the Luer joint 57 barely begins to move to the proximal side, but the projection 661A immediately comes into contact with the turnback distal end 575b. In this case, the first rotation knob 66 can no longer rotate left, and the movement of the Luer joint 57 is also stopped.

In the present modified example, the projection 661A enters between the turnback proximal end 575a and the turnback distal end 575b, and thereby the stylet 5 is in a restricted state such that the stylet 5 can be neither advanced nor retracted.

An external force in a direction along the central axis L is sometimes applied to the Luer joint 57 unintentionally. If the Luer joint 57 is pulled back to the proximal end side by the external force, the tissue-fastening tool 2 indwelled in the common bile duct is pulled back. However, in the modified example, the tissue-fastening tool 2 is prevented from being pulled back by an action of the first turnback groove 575. When the projection 661A is fitted into the first turnback groove 575, if an external force toward the proximal side along the central axis L is applied to the Luer joint 57, the turnback distal end 575b comes into contact with the projection 661A, and thus the Luer joint 57 no longer moves to the proximal side. In contrast, when an external force toward the distal end side along the central axis L is applied to the Luer joint 57, the turnback proximal end 575a comes into contact with the projection 661A, and thus the Luer joint 57 no longer moves to the distal end side. That is, when the projection 661A is fitted into the first turnback groove 575, even if the external force in the direction of either the distal end side or the proximal end side along the central axis L is applied to the Luer joint 57, a range of the movement of the projection 661A is restricted between the turnback proximal end 575a and the turnback distal end 575b. As described above, since the distance in the direction of the central axis L between the turnback proximal end 575a and the turnback distal end 575b is sufficiently short, the Luer joint 57 is not substantially advanced or retracted by an unintended external force.

For this reason, in the case of the present modified example, for example, in step S7 of the above embodiment, even if the unintended external force is applied to the Luer joint 57, the Luer joint 57 does not substantially move due to the action of the first turnback groove 575. Therefore, the stylet 5 is restricted to allow neither the advancement nor the retraction. For this reason, the tissue-fastening tool 2 is prevented from being pulled back toward the needle tube 4 unintentionally.

Figure 29:
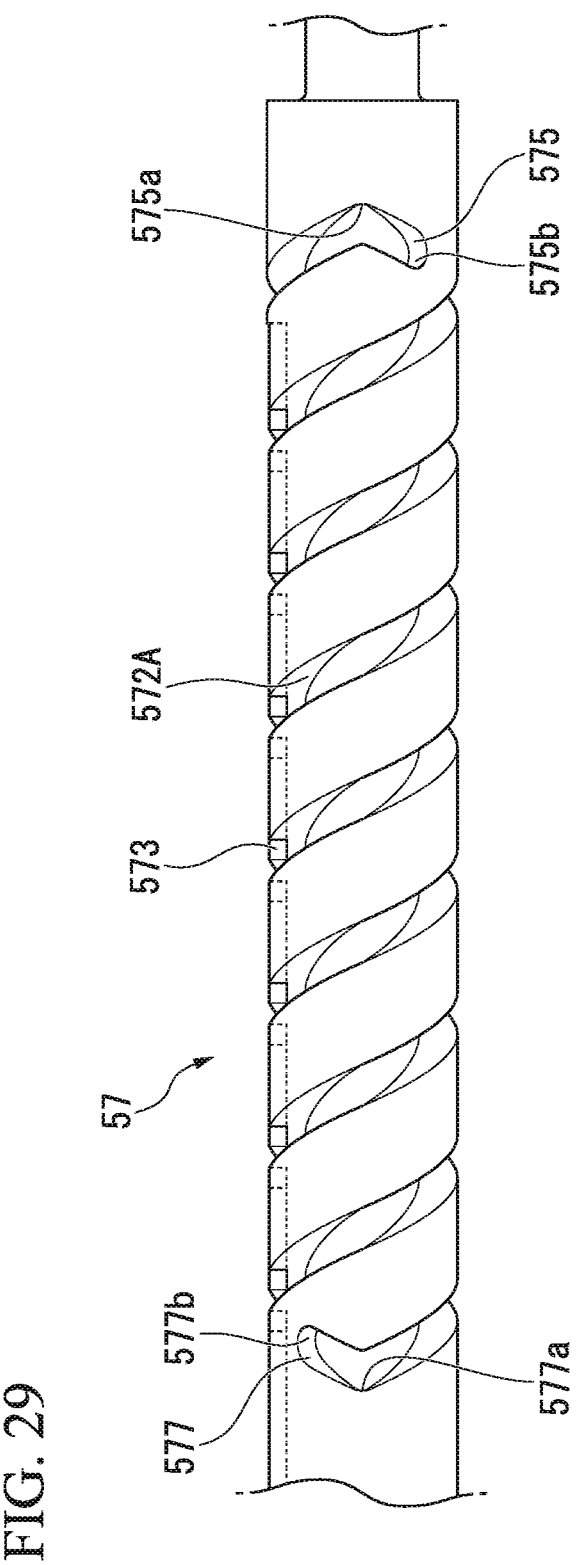
FIG. 29 is a view representing a modified example of the third screwing groove of the Luer joint of FIG. 27.

As represented in FIG. 29, the turnback groove may also be formed in the proximal end of the third helical groove 572A as well as the distal end of the third helical groove 572A. In this case, the turnback groove formed in the distal end side is referred to as a second turnback groove 577 that is bent and turned back such that a groove extends from the distal end toward the proximal end side of the third helical groove 572A. Like the first turnback groove 575, the second turnback groove 577 is bent such that the groove extends from the distal end toward the proximal end side of the third helical groove 572A, and has a distal end face (a turnback distal end) 577a of the third helical groove 572A, and a turnback proximal end (a second locking surface) 577b located at more proximal side than the distal end face. A length between the turnback proximal end 577b and the distal end face (the turnback distal end) 577a is sufficiently short over the full length of the third helical groove 572A. Therefore, a distance in the direction of the central axis L between the turnback proximal end 577b and the distal end face (the turnback distal end) 577a is also sufficiently short.

When the projection 661A is fitted into the second turnback groove 577, if an external force toward the distal side along the central axis L is applied to the Luer joint 57, the distal end face (the turnback distal end) 577a comes into contact with the projection 661A, and thus the Luer joint 57 no longer moves to the distal side. In contrast, when an external force toward the proximal side along the central axis L is applied to the Luer joint 57, the turnback proximal end 577b comes into contact with the projection 661A, and thus the Luer joint 57 no longer moves to the proximal end side. That is, when the projection 661A is fitted into the second turnback groove 577, even if the external force in the direction of either the distal end side or the proximal end side along the central axis L is applied to the Luer joint 57, the range of the movement of the projection 661A is restricted between the turnback proximal end 577b and the distal end face (the turnback distal end) 577a. As described above, since the distance in the direction of the central axis L between the turnback proximal end 577b and the distal end face (the turnback distal end) 577a is sufficiently short, the Luer joint 57 is not substantially advanced or retracted by an unintended external force. Therefore, in the second turnback groove 577, like the first turnback groove 575, the projection 661A enters between the turnback proximal end 577b and the distal end face (the turnback distal end) 577a, and thereby the stylet 5 is restricted to allow neither the advancement nor the retraction.

For this reason, in the case of the present modified example, for example, in step S6 of the above embodiment, although the unintended external force is applied to the Luer joint 57, the Luer joint 57 does not substantially move due to the action of the second turnback groove 577. Therefore, even in this case, the stylet 5 is restricted to allow neither the advancement nor the retraction. For this reason, the tissue-fastening tool 2 is prevented from being pushed out of the needle tube 4 unintentionally.

In the modified example, a method of restricting the movement of the Luer joint 57 in the direction of the central axis L is different from that of the above embodiment. As described above, in the modified example, the projection 661A is configured to be fitted into the third helical groove 572A, and the opposite ends 575a and 575b of the third helical groove 572A (the end portions of the turnback grooves 575 and 577 when the turnback grooves 575 and 577 are provided) and the projection 661A come into contact with each other. Thereby, the rotation of the first rotation knob 66 is restricted, and the movement of the Luer joint 57 is stopped. In contrast, in the above embodiment, the movement of the Luer joint 57 toward the distal side is restricted by contacting the proximal end side end face of the linear groove 573 of the Luer joint 57 with the proximal end side end face of the engaging projection 643b of the needle slider end member 643. In addition, the movement of the Luer joint 57 toward the proximal side is restricted by that the female screw 661 reaches the distal end side terminal of the male screw 572 of the Luer joint 57 which is threadedly engaged with the female screw 661.

<Third Modified Example>

Figure 30:
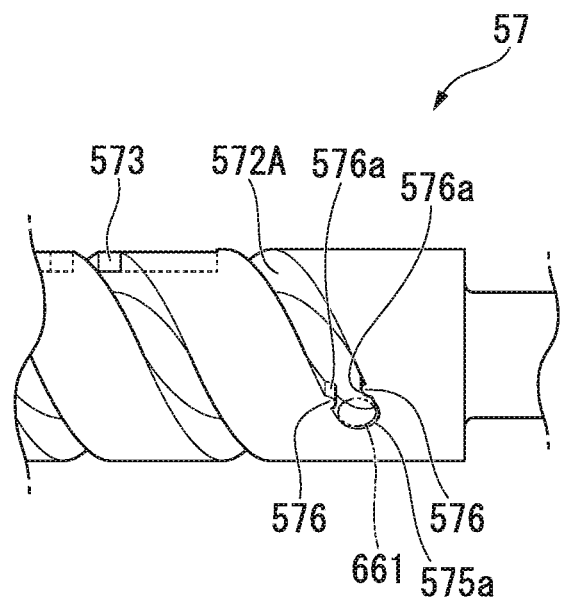
FIG. 30 is a view representing a modified example of the proximal end portion of the third screwing groove of the Luer joint of FIG. 27.

Further, as represented in FIG. 30, the first turnback groove 575 described above may be replaced with a structure constitutes with a pair of protrusions 576. The pair of protrusions 576 has locking surfaces 576a (surfaces extending in a direction intersecting the third helical groove 572A) that protrude to opposite to each other across a central axis of the third helical groove 572A at a position closer to the distal end side of the third helical groove 572A than the proximal end face 575a thereof. To be specific, proximal end portions of the pair of protrusions 576 are continuous with inner walls of the third helical groove 572A, and distal end portions of the pair of protrusions 576 are formed to face each other across the central axis of the third helical groove 572A. An interval between the distal end portions of the pair of protrusions 576 is slightly smaller than an outer diameter of the projection 661A. In addition, at least one of the Luer joint 57 or the projection 661A is formed of a resin. Thereby, when the projection 661A of the first rotation knob 66 moves to the proximal end of the third helical groove 572A, the projection 661A of the first rotation knob 66 passes over the pair of protrusions, and then enters between the proximal end face 575a and the pair of protrusions 576. Then, like the first turnback groove 575 described above, the stylet 5 is restricted to allow neither the advancement nor the retraction.

Figure 31:
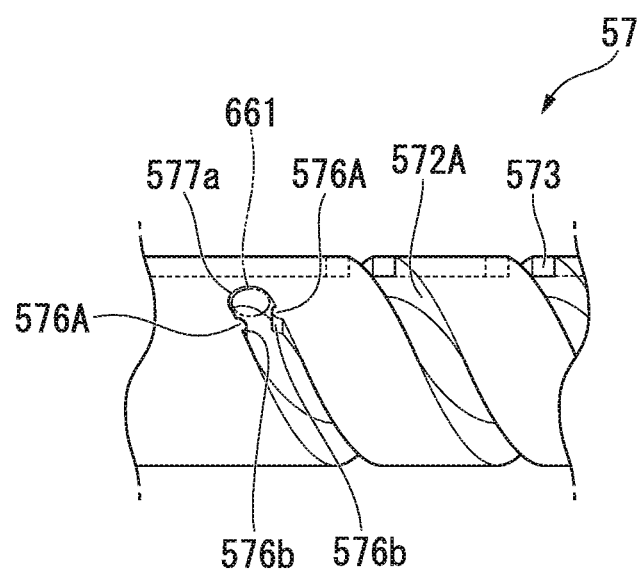
FIG. 31 is a view representing another modified example of the proximal end portion of the third screwing groove of the Luer joint of FIG. 27.

Further, as represented in FIG. 31, the second turnback groove 577 described above may be replaced with a structure constitutes with a pair of protrusions 576A. The pair of protrusions 576A has locking surfaces 576b (surfaces extending in a direction intersecting the third helical groove 572A) that protrude to opposite to each other across the central axis of the third helical groove 572A at a position closer to the proximal end side of the third helical groove 572A than the distal end face 577a thereof. To be specific, proximal end portions of the pair of protrusions 576A are continuous with the inner walls of the third helical groove 572A, and distal end portions of the pair of protrusions 576A are formed to face each other across the central axis of the third helical groove 572A. An interval between the distal end portions of the pair of protrusions 576A is slightly smaller than the outer diameter of the projection 661A. In addition, at least one of the Luer joint 57 or the projection 661A is formed of a resin. Thereby, when the projection 661A of the first rotation knob 66 moves to the distal end of the third helical groove 572A, the projection 661A of the first rotation knob 66 passes over the pair of protrusions 576A, and then enters between the distal end face 577a and the pair of protrusions 576A. Then, like the second turnback groove 577 described above, the stylet 5 is restricted to allow neither the advancement nor the retraction.

Even in this case, for example, in step S6 of the above embodiment, although the unintended external force is applied to the Luer joint 57, the Luer joint 57 does not substantially move due to the actions of the pair of protrusions 576A. Therefore, the stylet 5 is restricted to allow neither the advancement nor the retraction. For this reason, the tissue-fastening tool 2 is prevented from being pushed out of the needle tube 4 unintentionally. Similarly, in step S7 of the above embodiment, the tissue-fastening tool 2 is prevented from being pulled back toward the needle tube 4.

While the embodiments of the present invention have been described in detail with reference to the drawings, the specific configuration is not limited to the embodiments and includes design changes and the like within a scope that does not depart from the gist of the present invention.

Further, the constituent elements described in each of the embodiments and each of the modified examples can be constituted by appropriately combining them.

What is claimed is:

1. A tissue-fastening tool indwelling device comprising:
a sheath in which a lumen is formed;
a needle tube having a needle tip, formed in a tubular shape, and disposed to be projectable and retractable from a distal end of the lumen;
a tissue-fastening tool having a restoring force for restoration to a curved shape with distal and proximal end side regions and disposed inside the needle tube in a stretched state;
a stylet coupled to a proximal end portion of the tissue-fastening tool in the needle tube;
a needle slider configured to advance and retract the needle tube;
a first manipulation input part fixed to the needle slider in an advancing-retracting direction and configured to be rotatable with respect to the needle slider;
an intermediate member configured to advance with respect to the needle slider and configured to make the stylet to advance straight, in accordance with rotation of the first manipulation input part with respect to the needle slider; and
a restriction portion formed at the intermediate member and configured to restrict the rotation of the first manipulation input part,
wherein the stylet has:
a first state in which the stylet is advanced straight with respect to the needle tube and the sheath until the entire distal end side region of the tissue-fastening tool protrudes from the needle tube; and a second state in which the stylet is advanced while being rotated until a proximal end of the proximal end side region of the tissue-fastening tool protrudes from the needle tube after the stylet advanced with respect to the needle tube and the sheath, wherein:

in a restricted state in which the rotation of the first manipulation input part is restricted by the restriction portion, a distal end of the tissue-fastening tool protrudes from the needle tip, and a proximal end of the tissue-fastening tool is located in the needle tube, an outer circumference of the intermediate member has a step that helically extends between a proximal end and distal end of the intermediate member;

the first manipulation input part has a sliding portion that is slidable while being engaged with the step;

a proximal end face is formed at a terminal side of the step in a proximal end side of the intermediate member; and the restricted state is a state in which the sliding portion of the first manipulation input part abuts against the proximal end face and thereby the stylet is restricted not to be advanced.

2. The tissue-fastening tool indwelling device according to claim 1, comprising:

a second manipulation input part that advances the stylet while rotating the stylet with respect to the needle tube, wherein the first manipulation input part straightly advances the stylet with respect to the needle tube and the sheath.

3. The tissue-fastening tool indwelling device according to claim 2, comprising:

a cam tube that has a first helical groove which is formed helically on a wall surface of a cylinder and into which a proximal end region of the stylet is inserted;

the intermediate member having a distal end face fixed to a proximal end portion of the cam tube;

a guided part that is located at closer to a distal side than the distal end face of the intermediate member, and protrudes outward from an outer circumferential surface of the proximal end region of the stylet in a radial direction, the guided part being slidably engaged with the first helical groove; and a guide member that has a slit surface forming a slit extending along a longitudinal axis of the stylet in a linear shape to be engaged with the guided part, that is relative rotatable around a central axis of the needle tube with respect to the needle tube, and that is fixed to a proximal end portion of the needle tube in a direction of the central axis of the needle tube, wherein in the first state, the stylet straightly advances the tissue-fastening tool into the needle tube depending on input to the first manipulation input part, and in the second state, the stylet causes the guided part to slide along the first helical groove depending on input to the second manipulation input part and advances the tissue-fastening tool while rotating the tissue-fastening tool in the needle tube.

4. The tissue-fastening tool indwelling device according to claim 2, comprising:

a second cam tube that has an outer circumferential surface in which a fourth helical groove helically formed in a wall surface of a cylinder is formed, and has an end portion of the fourth helical groove on the outer circumferential surface; and a fitting hole which is formed in a region between grooves for the fourth helical groove on the outer circumferential surface of the second cam tube, the fitting hole into which a rod-like member is fittable;

wherein the second manipulation input part is a rotation handle having a second engaging part that protrudes inward from an inner circumferential surface thereof in a radial direction and that is slidably fitted into the fourth helical groove, and when the second engaging part is locked on an end portion of the fourth helical groove of the second cam tube, the fitting hole is exposed at a position closer to a distal side of the second cam tube than a distal end of the rotation handle.

5. The tissue-fastening tool indwelling device according to claim 2, wherein a maximum movable amount of the stylet in a direction along a longitudinal axis of the sheath due to manipulation of the first manipulation input part is set to be smaller than the maximum movable amount of the stylet in the direction along the longitudinal axis of the sheath due to manipulation of the second manipulation input part.

6. A tissue-fastening tool indwelling device comprising:

a sheath in which a lumen is formed;

a needle tube having a needle tip, formed in a tubular shape, and disposed to be projectable and retractable from a distal end of the lumen;

a tissue-fastening tool having a restoring force for restoration to a curved shape with distal and proximal end side regions and disposed inside the needle tube in a stretched state;

a stylet coupled to a proximal end portion of the tissue-fastening tool in the needle tube;

a needle slider configured to advance and retract the needle tube;

a first manipulation input part fixed to the needle slider in an advancing-retracting direction and configured to be rotatable with respect to the needle slider;

an intermediate member configured to advance with respect to the needle slider and configured to make the stylet to advance straight, in accordance with rotation of the first manipulation input part with respect to the needle slider; and a restriction portion formed at the intermediate member and configured to restrict the rotation of the first manipulation input part, wherein the stylet has:

a first state in which the stylet is advanced straight with respect to the needle tube and the sheath until the entire distal end side region of the tissue-fastening tool protrudes from the needle tube; and a second state in which the stylet is advanced while being rotated until a proximal end of the proximal end side region of the tissue-fastening tool protrudes from the needle tube after the stylet advanced with respect to the needle tube and the sheath, wherein:

in a restricted state in which the rotation of the first manipulation input part is restricted by the restriction portion, a distal end of the tissue-fastening tool protrudes from the needle tip, and a proximal end of the tissue-fastening tool is located in the needle tube;

an outer circumference of the intermediate member has a helical step that extends between a proximal end and distal end of the intermediate member;

the first manipulation input part has a sliding portion that is slidable while being engaged with the step;

a proximal end face is formed at a terminal side of the step in a proximal end side of the intermediate member;

a locking surface is formed at closer to a distal end side of the intermediate member than the proximal end face; and the restricted state is a state in which, the sliding portion of the first manipulation input part enters between the locking surface and the proximal end face, and thereby the stylet is restricted not to be advanced and retracted.

7. The tissue-fastening tool indwelling device according to claim 6, comprising a second manipulation input part that advances the stylet while rotating the stylet with respect to the needle tube, wherein the first manipulation input part straightly advances the stylet with respect to the needle tube and the sheath.

8. The tissue-fastening tool indwelling device according to claim 7, comprising:

a cam tube that has a first helical groove which is formed helically on a wall surface of a cylinder and into which a proximal end region of the stylet is inserted;

the intermediate member having a distal end face fixed to a proximal end portion of the cam tube;

a guided part that is located at closer to a distal side than the distal end face of the intermediate member, and protrudes outward from an outer circumferential surface of the proximal end region of the stylet in a radial direction, the guided part being slidably engaged with the first helical groove; and a guide member that has a slit surface forming a slit extending along a longitudinal axis of the stylet in a linear shape to be engaged with the guided part, that is relative rotatable around a central axis of the needle tube with respect to the needle tube, and that is fixed to a proximal end portion of the needle tube in a direction of the central axis of the needle tube, wherein in the first state, the stylet straightly advances the tissue-fastening tool into the needle tube depending on input to the first manipulation input part, and in the second state, the stylet causes the guided part to slide along the first helical groove depending on input to the second manipulation input part and advances the tissue-fastening tool while rotating the tissue-fastening tool in the needle tube.

9. The tissue-fastening tool indwelling device according to claim 7, comprising:

a second cam tube that has an outer circumferential surface in which a fourth helical groove helically formed in a wall surface of a cylinder is formed, and has an end portion of the fourth helical groove on the outer circumferential surface; and a fitting hole which is formed in a region between grooves for the fourth helical groove on the outer circumferential surface of the second cam tube, the fitting hole into which a rod-like member is fittable;

wherein the second manipulation input part is a rotation handle having a second engaging part that protrudes inward from an inner circumferential surface thereof in a radial direction and that is slidably fitted into the fourth helical groove, and when the second engaging part is locked on an end portion of the fourth helical groove of the second cam tube, the fitting hole is exposed at a position closer to a distal side of the second cam tube than a distal end of the rotation handle.

10. The tissue-fastening tool indwelling device according to claim 7, wherein a maximum movable amount of the stylet in a direction along a longitudinal axis of the sheath due to manipulation of the first manipulation input part is set to be smaller than the maximum movable amount of the stylet in the direction along the longitudinal axis of the sheath due to manipulation of the second manipulation input part.

11. A tissue-fastening tool indwelling device comprising:

a sheath in which a lumen is formed;

a needle tube having a needle tip, formed in a tubular shape, and disposed to be projectable and retractable from a distal end of the lumen;

a tissue-fastening tool having a restoring force for restoration to a curved shape with distal and proximal end side regions and disposed inside the needle tube in a stretched state;

a stylet coupled to a proximal end portion of the tissue-fastening tool in the needle tube;

a cam tube that has a first helical groove which is formed helically on a wall surface of a cylinder and into which a proximal end region of the stylet is inserted;

an intermediate member having a distal end face fixed to a proximal end portion of the cam tube;

a guided part that is located at closer to a distal side than the distal end face of the intermediate member, protrudes outward from an outer circumferential surface of the proximal end region of the stylet in a radial direction, and is slidably engaged with the first helical groove; and a guide member that has a slit surface forming a slit extending along a longitudinal axis of the stylet in a linear shape to be engaged with the guided part, that is relatively rotatable around a central axis of the needle tube with respect to the needle tube, and that is fixed to a proximal end portion of the needle tube in a direction of the central axis of the needle tube, wherein the stylet has:

a first state in which the stylet is advanced straight with respect to the needle tube and the sheath until the entire distal end side region of the tissue-fastening tool protrudes from the needle tube; and a second state in which the stylet is advanced while being rotated until a proximal end of the proximal end side region of the tissue-fastening tool protrudes from the needle tube after the stylet advanced with respect to the needle tube and the sheath, wherein, in the first state, the guided part comes into contact with the distal end face of the intermediate member, and as the guided part is pushed out by the distal end face of the intermediate member, the stylet is straightly advanced with respect to the needle tube and the sheath while causing the guided part to slide along the slit surface, and in the second state, the guided part is separated from the distal end face of the intermediate member, and as the stylet is rotated while being advanced with respect to the intermediate member, the guided part rotates while being engaged with the slit surface in a rotational direction of the stylet and while causing the guided part to slide along the first helical groove of the cam tube, and the guided part advances the stylet while rotating the stylet with respect to the needle tube.

12. The tissue-fastening tool indwelling device according to claim 11, comprising:

a needle slider fixed to the guide member with respect to a direction of a longitudinal axis of the guide member so as to be rotatable with respect to the guide member;

a main manipulation part main body provided between the guide member and the needle slider in a radial direction of the needle slider and having an outer circumferential surface in which a second helical groove formed in a helical shape is formed; and a slide button unit having a base body and a locking part that protrudes inward in a radial direction of the base body to be engaged with the second helical groove, wherein a dent portion is formed at a proximal end of the second helical groove, and the locking part is fitted into the dent portion and is locked in a helical direction of the second helical groove.

13. The tissue-fastening tool indwelling device according to claim 11, comprising:

a needle slider fixed to the guide member with respect to a direction of a longitudinal axis of the guide member so as to be rotatable with respect to the guide member; and a first manipulation input part that straightly advances the stylet with respect to the needle tube and the sheath, wherein:

the first manipulation input part is a rotation knob that is rotatable with respect to the needle slider;

the rotation knob has a projection protruding inward in a radial direction from an inner circumference thereof;

a third helical groove and a first locking surface that formed at a proximal end portion of the third helical groove are provided with an outer circumference of the intermediate member, the third helical groove into which the projection slides while being engaged with the third helical groove; and if an external force toward the proximal end side is applied to the intermediate member when the projection is located at closer to a proximal side of the third helical groove than the first locking surface, the first locking surface locks the projection.

14. The tissue-fastening tool indwelling device according to claim 11, comprising:

a needle slider fixed to the guide member with respect to a direction of a longitudinal axis of the guide member so as to be rotatable with respect to the guide member; and a first manipulation input part that straightly advances the stylet with respect to the needle tube and the sheath, wherein:

the first manipulation input part is a rotation knob that is rotatable with respect to the needle slider;

the rotation knob has a projection protruding inward in a radial direction from an inner circumference thereof;

a third helical groove and a second locking surface formed at a distal end portion of the third helical groove are provided with an outer circumference of the intermediate member, the third helical groove into which the projection slides while being engaged with the third helical groove; and if an external force toward the distal end side is applied to the intermediate member when the projection is located at closer to a distal end side of the third helical groove than the second locking surface, the second locking surface locks the projection.

* * * * *